(12) United States Patent
Clauson et al.

(10) Patent No.: US 9,763,829 B2
(45) Date of Patent: Sep. 19, 2017

(54) FLOW PROMOTING OCULAR IMPLANT

(71) Applicant: Novartis AG, Basel (CH)

(72) Inventors: Luke Clauson, Menlo Park, CA (US);
Steven John, Menlo Park, CA (US);
David Lari, Menlo Park, CA (US);
Sean Ianchulev, Menlo Park, CA (US);
Michael Schaller, Menlo Park, CA (US)

(73) Assignee: Novartis AG, Basel (CH)

( * ) Notice: Subject to any disclaimer, the term of this patent is extended or adjusted under 35 U.S.C. 154(b) by 9 days.

(21) Appl. No.: 14/078,206

(22) Filed: Nov. 12, 2013

(65) Prior Publication Data
US 2014/0135916 A1    May 15, 2014

Related U.S. Application Data

(60) Provisional application No. 61/726,477, filed on Nov. 14, 2012.

(51) Int. Cl.
*A61M 5/00*      (2006.01)
*A61F 9/007*      (2006.01)

(52) U.S. Cl.
CPC .............................. *A61F 9/00781* (2013.01)

(58) Field of Classification Search
CPC ................ A61F 9/00781; A61F 9/0017; A61F 9/00772; A61F 11/002; A61M 27/002
See application file for complete search history.

(56) References Cited

U.S. PATENT DOCUMENTS

| | | | |
|---|---|---|---|
| 2,990,670 A | 7/1961 | Kingsbury |
| 3,439,675 A | 4/1969 | Cohen |
| 3,767,759 A | 10/1973 | Wichterle |
| 3,788,327 A | 1/1974 | Donowitz et al. |
| 3,915,172 A | 10/1975 | Wichterle et al. |
| 4,037,604 A | 7/1977 | Newkirk |
| 4,402,681 A | 9/1983 | Haas et al. |
| 4,457,757 A | 7/1984 | Molteno |
| 4,521,210 A | 6/1985 | Wong |

(Continued)

FOREIGN PATENT DOCUMENTS

| | | |
|---|---|---|
| CN | 1225027 A | 8/1999 |
| CN | 1285724 A | 2/2001 |

(Continued)

OTHER PUBLICATIONS

Barsky et al. "Evaluation of absorbable gelatin film (Gelfilm) in cyclodialysis clefts" Arch. Ophth. 60(6): 1044-1052,1958.

(Continued)

*Primary Examiner* — Melanie Tyson
(74) *Attorney, Agent, or Firm* — Mintz Levin Cohn Ferris Glovsky and Popeo, P.C.

(57) ABSTRACT

Disclosed are devices, methods and systems for treatment of eye disease, including open angle glaucoma and narrow angle glaucoma. Implants are described herein that create a directed flow field, such as between the anterior chamber and either the supraciliary space or suprachoroidal space. In addition, the implant can include a variety of features, including extruded features, such as rings and pegs, which can assist in preventing ocular tissue from collapsing onto the implant and occluding fluid pathways.

12 Claims, 7 Drawing Sheets

(56) References Cited

U.S. PATENT DOCUMENTS

| | | |
|---|---|---|
| 4,554,918 A | 11/1985 | White |
| 4,604,087 A | 8/1986 | Joseph |
| 4,617,715 A | 10/1986 | Koistinen et al. |
| 4,634,418 A | 1/1987 | Binder |
| 4,722,724 A | 2/1988 | Schocket |
| 4,750,901 A | 6/1988 | Molteno |
| 4,787,885 A | 11/1988 | Binder |
| 4,826,478 A | 5/1989 | Schocket |
| 4,846,172 A | 7/1989 | Berlin |
| 4,863,457 A | 9/1989 | Lee |
| 4,886,488 A | 12/1989 | White |
| 4,900,300 A | 2/1990 | Lee |
| 4,946,436 A | 8/1990 | Smith |
| 4,968,296 A | 11/1990 | Ritch et al. |
| 5,041,081 A | 8/1991 | Odrich |
| 5,071,408 A | 12/1991 | Ahmed |
| 5,073,163 A | 12/1991 | Lippman |
| 5,092,837 A | 3/1992 | Ritch et al. |
| 5,127,901 A | 7/1992 | Odrich |
| 5,171,213 A | 12/1992 | Price, Jr. |
| 5,178,604 A | 1/1993 | Baerveldt et al. |
| 5,180,362 A | 1/1993 | Worst |
| 5,284,476 A | 2/1994 | Koch |
| 5,300,020 A | 4/1994 | L'Esperance, Jr. |
| 5,338,291 A | 8/1994 | Speckman et al. |
| 5,342,370 A | 8/1994 | Simon et al. |
| 5,346,464 A | 9/1994 | Camras |
| 5,370,607 A | 12/1994 | Memmen |
| 5,372,577 A | 12/1994 | Ungerleider |
| 5,397,300 A | 3/1995 | Baerveldt et al. |
| 5,423,777 A | 6/1995 | Tajiri et al. |
| 5,433,701 A | 7/1995 | Rubinstein |
| 5,443,505 A | 8/1995 | Wong et al. |
| 5,454,746 A | 10/1995 | Guegan et al. |
| 5,476,445 A | 12/1995 | Baerveldt et al. |
| 5,558,629 A | 9/1996 | Baerveldt et al. |
| 5,558,630 A | 9/1996 | Fisher |
| 5,569,197 A * | 10/1996 | Helmus .............. A61M 25/09 604/102.02 |
| RE35,390 E | 12/1996 | Smith |
| 5,601,094 A | 2/1997 | Reiss |
| 5,626,558 A | 5/1997 | Suson |
| 5,626,559 A | 5/1997 | Solomon |
| 5,651,782 A | 7/1997 | Simon et al. |
| 5,676,944 A | 10/1997 | Alvarado et al. |
| 5,702,414 A | 12/1997 | Richter et al. |
| 5,704,907 A | 1/1998 | Nordquist et al. |
| 5,713,844 A | 2/1998 | Peyman |
| 5,741,292 A | 4/1998 | Mendius |
| 5,743,868 A | 4/1998 | Brown et al. |
| 5,749,879 A | 5/1998 | Middleman et al. |
| 5,752,928 A | 5/1998 | de Roulhac et al. |
| 5,792,075 A | 8/1998 | Schwager |
| 5,807,244 A | 9/1998 | Barot |
| 5,807,302 A | 9/1998 | Wandel |
| 5,868,697 A | 2/1999 | Richter et al. |
| 5,882,327 A | 3/1999 | Jacob |
| 5,893,837 A | 4/1999 | Eagles et al. |
| 5,941,250 A | 8/1999 | Aramant et al. |
| 5,968,058 A | 10/1999 | Richter et al. |
| 6,007,510 A | 12/1999 | Nigam |
| 6,007,511 A | 12/1999 | Prywes |
| 6,036,678 A | 3/2000 | Giungo |
| 6,050,970 A | 4/2000 | Baerveldt |
| 6,050,999 A | 4/2000 | Paraschac et al. |
| 6,077,299 A | 6/2000 | Adelberg et al. |
| 6,102,045 A | 8/2000 | Nordquist et al. |
| 6,142,969 A | 11/2000 | Nigam |
| 6,152,918 A | 11/2000 | Padilla et al. |
| 6,174,307 B1 | 1/2001 | Daniel et al. |
| 6,186,974 B1 | 2/2001 | Allan et al. |
| 6,203,513 B1 | 3/2001 | Yaron et al. |
| 6,221,078 B1 | 4/2001 | Bylsma |
| 6,251,090 B1 | 6/2001 | Avery et al. |
| 6,261,256 B1 | 7/2001 | Ahmed |
| 6,264,668 B1 | 7/2001 | Prywes |
| 6,270,472 B1 | 8/2001 | Antaki et al. |
| 6,331,313 B1 | 12/2001 | Wong et al. |
| 6,375,642 B1 | 4/2002 | Grieshaber et al. |
| 6,383,219 B1 | 5/2002 | Telandro et al. |
| 6,450,984 B1 | 9/2002 | Lynch et al. |
| 6,464,724 B1 | 10/2002 | Lynch et al. |
| 6,468,283 B1 | 10/2002 | Richter et al. |
| 6,471,666 B1 | 10/2002 | Odrich |
| 6,471,777 B1 | 10/2002 | Kobayashi et al. |
| 6,494,857 B1 | 12/2002 | Neuhann |
| 6,508,779 B1 | 1/2003 | Suson |
| 6,510,600 B2 | 1/2003 | Yaron et al. |
| 6,524,275 B1 | 2/2003 | Lynch et al. |
| 6,533,768 B1 | 3/2003 | Hill |
| 6,537,568 B2 | 3/2003 | Olejnik et al. |
| 6,544,208 B2 | 4/2003 | Ethier et al. |
| 6,544,249 B1 | 4/2003 | Yu et al. |
| 6,558,342 B1 | 5/2003 | Yaron et al. |
| 6,561,974 B1 | 5/2003 | Grieshaber et al. |
| 6,579,256 B2 | 6/2003 | Hughes |
| 6,589,203 B1 | 7/2003 | Mitrev |
| 6,595,945 B2 | 7/2003 | Brown |
| 6,626,858 B2 | 9/2003 | Lynch et al. |
| 6,638,239 B1 | 10/2003 | Bergheim et al. |
| 6,648,283 B2 | 11/2003 | Chase et al. |
| 6,666,841 B2 | 12/2003 | Gharib et al. |
| 6,676,607 B2 | 1/2004 | de Juan, Jr. et al. |
| 6,699,210 B2 | 3/2004 | Williams et al. |
| 6,699,211 B2 | 3/2004 | Savage |
| 6,719,750 B2 | 4/2004 | Varner et al. |
| 6,726,664 B2 | 4/2004 | Yaron et al. |
| 6,726,676 B2 | 4/2004 | Stegmann et al. |
| 6,730,056 B1 | 5/2004 | Ghaem et al. |
| 6,736,791 B1 | 5/2004 | Tu et al. |
| 6,741,666 B1 | 5/2004 | Henry et al. |
| 6,752,753 B1 | 6/2004 | Hoskins et al. |
| 6,780,164 B2 | 8/2004 | Bergheim et al. |
| 6,783,544 B2 | 8/2004 | Lynch et al. |
| 6,786,888 B1 | 9/2004 | Zadno-Azizi et al. |
| 6,827,699 B2 | 12/2004 | Lynch et al. |
| 6,827,700 B2 | 12/2004 | Lynch et al. |
| 6,881,197 B1 | 4/2005 | Nigam |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,966,888 B2 | 11/2005 | Cullen et al. |
| 6,969,384 B2 | 11/2005 | de Juan, Jr. et al. |
| 6,981,958 B1 | 1/2006 | Gharib et al. |
| 6,989,007 B2 | 1/2006 | Shadduck |
| 7,041,077 B2 | 5/2006 | Shields |
| 7,090,681 B2 | 8/2006 | Weber et al. |
| 7,094,225 B2 | 8/2006 | Tu et al. |
| 7,135,009 B2 | 11/2006 | Tu et al. |
| 7,160,264 B2 | 1/2007 | Lisk, Jr. et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,195,774 B2 | 3/2007 | Carvalho et al. |
| 7,207,965 B2 | 4/2007 | Simon |
| 7,220,238 B2 | 5/2007 | Lynch et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,431,710 B2 | 10/2008 | Tu et al. |
| 7,488,303 B1 | 2/2009 | Haffner et al. |
| 7,563,241 B2 | 7/2009 | Tu et al. |
| 7,708,711 B2 | 5/2010 | Tu et al. |
| 7,850,637 B2 | 12/2010 | Lynch et al. |
| 7,857,782 B2 | 12/2010 | Tu et al. |
| 7,867,186 B2 | 1/2011 | Haffner et al. |
| 7,867,205 B2 | 1/2011 | Bergheim et al. |
| 7,972,616 B2 | 7/2011 | Dubrow et al. |
| 8,075,511 B2 | 12/2011 | Tu et al. |
| 8,128,588 B2 | 3/2012 | Coroneo |
| 8,172,899 B2 | 5/2012 | Silvestrini et al. |
| 8,337,393 B2 | 12/2012 | Silverstrini et al. |

(56) References Cited

U.S. PATENT DOCUMENTS

| | | |
|---|---|---|
| 8,702,727 B1 | 4/2014 | Harrington et al. |
| 8,721,656 B2 | 5/2014 | De Juan, Jr. et al. |
| 2002/0013546 A1 | 1/2002 | Grieshaber et al. |
| 2002/0013572 A1 | 1/2002 | Berlin |
| 2002/0072673 A1 | 6/2002 | Yamamoto et al. |
| 2002/0087111 A1 | 7/2002 | Ethier et al. |
| 2002/0111608 A1 | 8/2002 | Baerveldt et al. |
| 2002/0128613 A1 | 9/2002 | Nakayama |
| 2002/0133168 A1 | 9/2002 | Smedley et al. |
| 2002/0143284 A1 | 10/2002 | Tu et al. |
| 2002/0177856 A1 | 11/2002 | Richter et al. |
| 2002/0188308 A1 | 12/2002 | Tu et al. |
| 2002/0193725 A1 | 12/2002 | Odrich |
| 2002/0193804 A1 | 12/2002 | Tickle |
| 2003/0028127 A1 | 2/2003 | Balzum et al. |
| 2003/0028228 A1 | 2/2003 | Sand |
| 2003/0055372 A1 | 3/2003 | Lynch et al. |
| 2003/0060752 A1 | 3/2003 | Bergheim et al. |
| 2003/0097151 A1 | 5/2003 | Smedley et al. |
| 2003/0097171 A1 | 5/2003 | Elliott |
| 2003/0109883 A1 | 6/2003 | Matsuzaki et al. |
| 2003/0135149 A1 | 7/2003 | Cullen et al. |
| 2003/0181848 A1 | 9/2003 | Bergheim et al. |
| 2003/0187384 A1 | 10/2003 | Bergheim et al. |
| 2003/0208163 A1 | 11/2003 | Yaron et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0015140 A1 | 1/2004 | Shields |
| 2004/0024345 A1 | 2/2004 | Gharib et al. |
| 2004/0088048 A1 | 5/2004 | Richter et al. |
| 2004/0092856 A1 | 5/2004 | Dahan |
| 2004/0097984 A1 | 5/2004 | Zapata |
| 2004/0102729 A1 | 5/2004 | Haffner et al. |
| 2004/0106977 A1 | 6/2004 | Sullivan et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0148022 A1 | 7/2004 | Eggleston |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225250 A1 | 11/2004 | Yablonski |
| 2004/0236343 A1 | 11/2004 | Taylor et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260228 A1 | 12/2004 | Lynch et al. |
| 2005/0008673 A1 | 1/2005 | Snyder et al. |
| 2005/0049578 A1 | 3/2005 | Tu et al. |
| 2005/0085892 A1 | 4/2005 | Goto et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0119737 A1 | 6/2005 | Bene et al. |
| 2005/0125003 A1 | 6/2005 | Pinchuk et al. |
| 2005/0143817 A1 | 6/2005 | Hunter et al. |
| 2005/0149080 A1 | 7/2005 | Hunter et al. |
| 2005/0171507 A1 | 8/2005 | Christian et al. |
| 2005/0175663 A1 | 8/2005 | Hunter et al. |
| 2005/0181011 A1 | 8/2005 | Hunter et al. |
| 2005/0181977 A1 | 8/2005 | Hunter et al. |
| 2005/0182350 A1 | 8/2005 | Nigam |
| 2005/0191331 A1 | 9/2005 | Hunter et al. |
| 2005/0192527 A1 | 9/2005 | Gharib et al. |
| 2005/0197613 A1 | 9/2005 | Sniegowski et al. |
| 2005/0209549 A1 | 9/2005 | Bergheim et al. |
| 2005/0209550 A1 | 9/2005 | Bergheim et al. |
| 2005/0232972 A1 | 10/2005 | Odrich |
| 2005/0244462 A1 | 11/2005 | Farooq |
| 2005/0250788 A1 | 11/2005 | Tu et al. |
| 2005/0266047 A1 | 12/2005 | Tu et al. |
| 2005/0267397 A1 | 12/2005 | Bhalla |
| 2005/0267398 A1 | 12/2005 | Protopsaltis et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0283108 A1 | 12/2005 | Savage |
| 2005/0287188 A1 | 12/2005 | Anderson et al. |
| 2005/0288617 A1 | 12/2005 | Yaron et al. |
| 2005/0288619 A1 | 12/2005 | Gharib et al. |
| 2006/0004348 A1 | 1/2006 | Scheller et al. |
| 2006/0020248 A1 | 1/2006 | Prescott |
| 2006/0032507 A1 | 2/2006 | Tu |
| 2006/0036207 A1 | 2/2006 | Koonmen et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0116626 A1 | 6/2006 | Smedley et al. |
| 2006/0149194 A1 | 7/2006 | Conston et al. |
| 2006/0155238 A1 | 7/2006 | Shields |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0235367 A1 | 10/2006 | Takashima et al. |
| 2006/0241580 A1 | 10/2006 | Mittelstein et al. |
| 2006/0241749 A1 | 10/2006 | Tu et al. |
| 2006/0276739 A1 | 12/2006 | Brown |
| 2007/0010827 A1 | 1/2007 | Tu et al. |
| 2007/0088242 A1 | 4/2007 | Coroneo |
| 2007/0088424 A1 | 4/2007 | Greenberg et al. |
| 2007/0088432 A1 | 4/2007 | Solovay et al. |
| 2007/0106235 A1 | 5/2007 | Coroneo |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0129717 A1 | 6/2007 | Brown et al. |
| 2007/0141106 A1 | 6/2007 | Bonutti et al. |
| 2007/0149915 A1 | 6/2007 | Yablonski |
| 2007/0191863 A1 | 8/2007 | De Juan et al. |
| 2007/0207186 A1 | 9/2007 | Scanlon et al. |
| 2007/0233037 A1 | 10/2007 | Gifford, et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2008/0015488 A1 | 1/2008 | Tu et al. |
| 2008/0045878 A1 | 2/2008 | Bergheim et al. |
| 2008/0058704 A1 | 3/2008 | Hee et al. |
| 2008/0108933 A1 | 5/2008 | Yu et al. |
| 2008/0147021 A1* | 6/2008 | Jani .................. 604/288.01 |
| 2008/0195027 A1 | 8/2008 | Coroneo |
| 2008/0200860 A1 | 8/2008 | Tu et al. |
| 2008/0228127 A1* | 9/2008 | Burns ............... A61F 9/00781 604/9 |
| 2008/0234624 A2 | 9/2008 | Bergheim et al. |
| 2009/0036819 A1 | 2/2009 | Tu et al. |
| 2009/0036840 A1 | 2/2009 | Viray et al. |
| 2009/0043321 A1 | 2/2009 | Conston et al. |
| 2009/0118702 A1 | 5/2009 | Lazar |
| 2009/0171358 A1 | 7/2009 | Chang et al. |
| 2009/0182421 A1 | 7/2009 | Silvestrini et al. |
| 2010/0010416 A1 | 1/2010 | Juan, Jr. et al. |
| 2010/0134759 A1 | 6/2010 | Silvestrini et al. |
| 2010/0137981 A1 | 6/2010 | Silvestrini et al. |
| 2010/0152641 A1 | 6/2010 | Yablonski |
| 2010/0211079 A1 | 8/2010 | Aramant |
| 2010/0234790 A1 | 9/2010 | Tu et al. |
| 2010/0274259 A1 | 10/2010 | Yaron et al. |
| 2011/0028883 A1 | 2/2011 | Juan, Jr. et al. |
| 2011/0028884 A1 | 2/2011 | Theodore Coroneo |
| 2011/0087148 A1 | 4/2011 | Silvestrini et al. |
| 2011/0087149 A1 | 4/2011 | Theodore Coroneo |
| 2011/0087150 A1 | 4/2011 | Theodore Coroneo |
| 2011/0087151 A1 | 4/2011 | Theodore Coroneo |

(56) References Cited

U.S. PATENT DOCUMENTS

| | | |
|---|---|---|
| 2011/0098629 A1 | 4/2011 | Juan, Jr. et al. |
| 2011/0098809 A1 | 4/2011 | Wardle et al. |
| 2011/0112546 A1 | 5/2011 | Juan, Jr. et al. |
| 2011/0238075 A1 | 9/2011 | Clauson et al. |
| 2011/0276054 A1 | 11/2011 | Helmy |
| 2011/0288525 A1* | 11/2011 | Hallen et al. ............... 604/506 |
| 2011/0306915 A1 | 12/2011 | De Juan, Jr. et al. |
| 2012/0035524 A1 | 2/2012 | Silvestrini |
| 2012/0035525 A1 | 2/2012 | Silvestrini |
| 2012/0089071 A1* | 4/2012 | Oliver et al. .................. 604/8 |
| 2012/0116504 A1 | 5/2012 | Lyons et al. |
| 2012/0123316 A1 | 5/2012 | Horvath et al. |
| 2012/0123434 A1 | 5/2012 | Grabner et al. |
| 2012/0220917 A1 | 8/2012 | Silvestrini et al. |
| 2012/0271272 A1 | 10/2012 | Hammack et al. |
| 2013/0281817 A1 | 10/2013 | Schaller et al. |
| 2013/0281908 A1 | 10/2013 | Schaller et al. |
| 2014/0012279 A1 | 1/2014 | de Juan, Jr. et al. |
| 2014/0066831 A1 | 3/2014 | Silvestrini et al. |
| 2014/0081195 A1 | 3/2014 | Clauson et al. |
| 2014/0107556 A1 | 4/2014 | Silvestrini et al. |
| 2014/0155805 A1 | 6/2014 | Schaller et al. |
| 2014/0188030 A1 | 7/2014 | Coroneo |
| 2014/0213958 A1 | 7/2014 | Clauson et al. |
| 2014/0309599 A1 | 10/2014 | Schaller |
| 2014/0323995 A1 | 10/2014 | Clauson et al. |
| 2014/0364789 A1 | 12/2014 | Schaller |
| 2014/0378886 A1 | 12/2014 | de Juan,, Jr. et al. |
| 2015/0022780 A1 | 1/2015 | John et al. |
| 2015/0126809 A1 | 5/2015 | Silvestrini et al. |
| 2015/0223982 A1 | 8/2015 | Yablonski |
| 2015/0238360 A1 | 8/2015 | de Juan, Jr. et al. |
| 2015/0320596 A1 | 11/2015 | Gifford, III et al. |
| 2015/0335487 A1 | 11/2015 | de Juan, Jr. |

FOREIGN PATENT DOCUMENTS

| | | |
|---|---|---|
| CN | 1124164 C | 10/2003 |
| CN | 1681457 A | 10/2005 |
| EP | 0228185 A1 | 11/1986 |
| EP | 1184010 A2 | 3/2002 |
| EP | 1310222 A2 | 5/2003 |
| EP | 1473004 A2 | 11/2004 |
| EP | 1477146 A2 | 11/2004 |
| EP | 1418868 B1 | 3/2008 |
| EP | 1977724 A1 | 10/2008 |
| EP | 2027837 A2 | 2/2009 |
| GB | 2101891 A | 1/1983 |
| JP | 2007-535386 A | 12/2007 |
| JP | 2010-533565 A | 10/2010 |
| RU | 2018289 C1 | 8/1994 |
| RU | 2056818 C1 | 3/1996 |
| RU | 2074686 C1 | 3/1997 |
| RU | 2074687 C1 | 3/1997 |
| RU | 2157678 C1 | 10/2000 |
| WO | WO-89/00869 A1 | 2/1989 |
| WO | WO-91/12046 A1 | 8/1991 |
| WO | WO-92/19294 A1 | 11/1992 |
| WO | WO-94/02081 A1 | 2/1994 |
| WO | WO-94/09721 A1 | 5/1994 |
| WO | WO-94/09837 A1 | 5/1994 |
| WO | WO-94/13234 A1 | 6/1994 |
| WO | WO-95/08310 A1 | 3/1995 |
| WO | WO-96/20742 A1 | 7/1996 |
| WO | WO-96/36377 A1 | 11/1996 |
| WO | WO-98/23237 A1 | 6/1998 |
| WO | WO-98/30181 A1 | 7/1998 |
| WO | WO-99/26567 A1 | 6/1999 |
| WO | WO 99/26567 A1 | 6/1999 |
| WO | WO-00/06223 A1 | 2/2000 |
| WO | WO-00/64389 A1 | 11/2000 |
| WO | WO-00/64390 A1 | 11/2000 |
| WO | WO-00/64391 A1 | 11/2000 |
| WO | WO-00/64393 A1 | 11/2000 |
| WO | WO-00/64511 A1 | 11/2000 |
| WO | WO-01/78631 A2 | 10/2001 |
| WO | WO-01/78656 A2 | 10/2001 |
| WO | WO-01/97727 A1 | 12/2001 |
| WO | WO-02/36052 A1 | 5/2002 |
| WO | WO-02/070045 A1 | 9/2002 |
| WO | WO-02/074052 A2 | 9/2002 |
| WO | WO-02/080811 A2 | 10/2002 |
| WO | WO-02/080829 A2 | 10/2002 |
| WO | WO-02/087418 A2 | 11/2002 |
| WO | WO-02/087479 A2 | 11/2002 |
| WO | WO-02/089699 A2 | 11/2002 |
| WO | WO-02/102274 A2 | 12/2002 |
| WO | WO-03/015659 A2 | 2/2003 |
| WO | WO-03/015667 A1 | 2/2003 |
| WO | WO-03/041622 A2 | 5/2003 |
| WO | WO-03/073968 A2 | 9/2003 |
| WO | WO-03/099175 A1 | 12/2003 |
| WO | WO-2004/014218 A2 | 2/2004 |
| WO | WO-2004/026106 A2 | 4/2004 |
| WO | WO-2004/026347 A2 | 4/2004 |
| WO | WO-2004/043231 A2 | 5/2004 |
| WO | WO-2004/056294 A1 | 7/2004 |
| WO | WO-2004/060219 A1 | 7/2004 |
| WO | WO-2004/062469 A2 | 7/2004 |
| WO | WO-2004/073552 A2 | 9/2004 |
| WO | WO-2004/110391 A2 | 12/2004 |
| WO | WO-2005/016418 A1 | 2/2005 |
| WO | WO-2005/046782 A1 | 5/2005 |
| WO | WO-2005/055873 A2 | 6/2005 |
| WO | WO-2005/105197 A2 | 11/2005 |
| WO | WO-2005/107664 A2 | 11/2005 |
| WO | WO-2005/107845 A1 | 11/2005 |
| WO | WO-2006/012421 A2 | 2/2006 |
| WO | WO-2006/036715 A2 | 4/2006 |
| WO | WO-2007/087061 A2 | 8/2007 |
| WO | WO-2007/115259 A2 | 10/2007 |
| WO | WO-2007/130393 A2 | 11/2007 |
| WO | WO-2008/061043 | 5/2008 |
| WO | WO-2009/012406 A1 | 1/2009 |
| WO | WO-2009/158524 A2 | 12/2009 |
| WO | WO-2010/065970 A1 | 6/2010 |
| WO | WO-2010/115101 A1 | 10/2010 |
| WO | WO 2014/078288 | 11/2013 |
| WO | WO 2014/190029 | 5/2014 |

OTHER PUBLICATIONS

Bick MW "Use of tantalum for ocular drainage" Arch Ophthal. 42(4): 373-88 (1949).

Bietti "The present state of the use of plastics in eye surgery" Acta Ophthalmol (Copenh) 33(4):337-70 (1955).

Brown et al., "Internal Sclerectomy for Glaucoma Filtering Surgery with an Automated Trephine," Archives of Ophthalmology, 105:133-136 (1987).

Burchfield JC, Kass MA, Wax MB. Primary valve malfunction of the Krupin eye valve with disk. J Glaucoma. Jun. 1997;6(3):152-6.

Chiou et al. "Ultrasound biomicroscopy of eyes undergoing deep sclerectomy with collagen implant" Br J Ophthalmol 80 (1996), pp. 541-544.

Chylack LT, Bellows AR. Molecular sieving in suprachoroidal fluid formation in man. Invest Ophthalmol Vis Sci 17: 420, 1978.

Classen et al. "A histopathologic and immunohistorchemical analysis of the filtration bleb after unsuccessful glaucoma seton implantation" Am. J. Ophthalmol. 122:205-12 (1996).

Cohen et al. "First day post-operative review following uncomplicated phacoemulsification" Eye 12(4):634-6 (1998).

Collaborative Normal-Tension Study Group. Comparison of glaucomatous progression between untreated patients with normal-tension glaucoma and patients with therapeutically reduced intraocular pressures. Am J Ophthalmol 1998;126:487-97.

Congdon N, O'Colmain B, Klaver CC, et al. Causes and prevalence of visual impairment among adults in the United States. Arch Ophthalmol 2004;122:477-85.

Coote. "Glaucoma Hollow Fiber Filters—A New Glaucoma Seton. Preliminary Results." *J. Glaucoma*. vol. 8 No. 1 Supplement (1999):p. S4.

(56) References Cited

OTHER PUBLICATIONS

Cullen, et al. "Anterior Chamber of Frontal Sinus Shunt for the Diversion of Aqueous Humor: A Pilot Study in Four Normal Dogs". *Veterinary Ophthalmology*. vol. 1. No. 1. (1998):31-39.

Demailly et al. "Non-penetrating deep sclerectomy (NPDS) with or without collagen device (CD) in primary open-angle glaucoma: middle-term retrospective study" International Ophthalmology 20: 131-140, 1997.

Derwent English abstract for EP 1184010, published Mar. 6, 2002 entitled: "Drainage unit for an eye, consists of a hollow line, a distribution member, and a pressure relief valve which only allows water to leave the eye chamber above a certain pressure," Accession No. 12409716 [351].

Dinakaran et al. "Is the first post-operative day review necessary following uncomplicated phacoemulsification surgery?" Eye, 14(3A):364-6 (2000).

Draeger "Chirurgische Maβnahmen bei kongenitalem Glaukom" (Surgical Interventions in Congenital Glaucoma) Klin Monatsbl Augenheilkd 1993; 202(5): 425-427 [Article in German with English summary included].

Einmahl et al. "Evaluation of a novel biomaterial in the suprachoroidal space of the rabbit eye" Invest Ophthalmol Vis Sci. 43:1533-1539 (2002).

Ellis, RA "A Reduction of Intraocular Pressure Using Plastics in Surgery" Am J Ophth. 50; 1960, 733-742.

Emi et al. "Hydrostatic pressure of the suprachoroidal space" Invest. Ophthal. Visual Sci. 30(2):233-238 (1989).

Fanous MM, Cohn RA. Propionibacterium endophthalmitis following Molteno tube repositioning. J Glaucoma. Aug. 1997;6(4):201-2.

Friedman DS, Wolfs RC, O'Colmain BJ, et al. Prevalence of open-angle glaucoma among adults in the United States. Arch Ophthalmol 2004;122:532-8.

Fuchs E. "Detachment of the choroid inadvertently during cataract surgery" [German] von Graefes Arch Ophthalmol, 51:199-224 (1900) [Article in German with English summary].

Gills et al. "Action of cyclodialysis utilizing an implant studied by manometry in a human eye" Exp Eye Res 1967; 6:75-78.

Gills JP "Cyclodialysis implants" South Med J. 1967 60(7):692-5.

Gills, "Cyclodialysis Implants in Human Eyes" Am J Ophth 61:1966,841-846.

Goldberg "Management of Uncontrolled Glaucoma With the Molteno System" Australian and New Zealand Journal of Ophthalmology 1987; 15: 97-107.

Gordon MO, Kass. MA, for the Ocular Hypertension Treatment Study Group. The Ocular Hypertension Treatment Study. Design and baseline description of the participants. Arch Ophthalmol 1999:573-83.

Grant, W.M. , MD, Further Studies on Facility of Flow Through the Trabecular Meshwork, A.M.A. Archives of Ophthalmololgy, Oct. 1958, vol. 60, pp. 523-533.

Gross et al. "Surgical therapy of chronic glaucoma in aphakia and pseudophakia" Ophthalmology, 95:1195-201 (1988).

Harper SL, Foster CS. Intraocular lens explantation in uveitis. Int Ophthalmol Clin. 2000 Winter; 40(1):107-16.

Harrington "Cataract and Glaucoma. Management of the coexistent conditions and a description of a new operation combining lens extraction with reverse cyclodialysis." Am J Ophthalmol. May 1996;61(5 Pt 2):1134-40.

Heijl A, Leske MC, Bengtsson B, et al for the Early Manifest Glaucoma Trial Group. Reduction of intraocular pressure and glaucoma progression. Results from the Early Manifest Glaucoma Trial. Arch Ophthalmol 2002;120:1268-79.

Heine I. "Cyclodialysis, a new glaucoma operation" [German] Dtsch Med Wochenschr, 31:824-826 (1905).

Hildebrand et al. "Efficacy of anterior chamber decompression in controlling early intraocular pressure spikes after uneventful phacoemulsification" J. Catact Refract Surg., 29:1087-92 (2003).

Hoskins, et al., "Aqueous Humor Outflow", Becker-Shaffer's Diagnosis and Therapy of the Glaucomas, 6th Edition, Chapter 4, pp. 41-66, 1989.

Howorth D J "Feasibility study for a micromachined glaucoma drainage device" Cranfield University School of industrial and manufacturing science MSc Thesis Academic Year 2001-2002 Sep. 13, 2002.

Hylton et al. "Update on prostaglandin analogs" Curr Opin Ophthalmol, 14:65-9 (2003).

Javitt JC, Chiang YP. Preparing for managed competition. Utilization of ambulatory eye care visits to ophthalmologists. Arch Ophthalmol 1993;111:1034-5.

Jay JL, Allan D. The benefit of early trabeculectomy versus conventional management in primary open-angle glaucoma relative to severity of disease. Eye 1989; 3:528-35.

Jordan J. "A Novel Approach to Suprachoroidal Drainage for the Surgical Treatment of Intractable Glaucoma" J. Glaucoma 15:200-205 (2006).

Jordan JF, Dietlein TS, Dinslage S, Luke C, Konen W, Krieglstein GK. Cyclodialysis ab inferno as a surgical approach to intractable glaucoma. Graefes Arch Clin Exp Ophthalmol. Aug. 2007;245(8):1071-6.

Karlen et al. "Deep sclerectomy with collagen implant: medium term results" Br. J. Ophthalmol, Jan. 1999, 83(1):6-11.

Kass MA, Heuer DK, Higginbotham EJ, et al for the Ocular Hypertension Treatment Study Group. The Ocular HypertensionTreatment Study. A randomized trial determines that topical ocular hypotensive medication delays or prevents the onset of primary open-angle glaucoma. Arch Ophthalmol 2002;120:701-13.

Klemm et al. "Die Ultraschallbiomikroskopie als Kriterium der Funktionsprüfung des suprachorioidalen Spaltes nach kammerwinkelchirurgischen Eingriffen (Ultrasound Biomicroscopic Imaging for Assessment of the Suprachoroidal Cleft after Angle Surgery) Klinische Monatsblätter für Augenheilkunde 1997; 210: 74-77 [Article in German with English summary included]".

Klemm et al. "Experimental use of space-retaining substances with extended duration: functional and morphological results" Graefes Arch Clin Exp Ophthalmol Sep. 1995; 233(9):592-7.

Kozlov et al. "Nonpenetrating deep sclerectomy with collagen" Eye microsurgery 3:44-46 (1990) [Russian with English translation].

Krejci "Cyclodialysis with hydroxymethyl methacrylate capillary strip (HCS). Animal experiments with a new approach in glaucoma drainage surgery" Ophthalmologica 1972; 164(2):113-21.

Krejcí L. "Microdrainage of anterior chamber of eye glaucoma operation using hydron capillary drain. " Acta Univ Carol Med Monogr. 1974;(61):1-90.

Kupfer "Studies on intraocular pressure. I. A technique for polyethylene tube implantation into the anterior chamber of the rabbit. " Arch Ophthalmol. Apr. 1961;65:565-70.

La Rocca "Gonioplasty in Glaucoma A Preliminary Report" Br J Ophth 46:1962, 404-415.

Law et al., "Retinal Complications After Aqueous Shunt Surgical Procedures for Glaucoma" Arch Ophthal.; Dec. 1996; vol. 114:1473-1480.

Lee et al. "Aqueous-venous shunt and intraocular pressure. Preliminary report of animal studies." *Investigative Ophthalmology*. vol. 5 No. 1: 59-64. Feb. 1966.

Lee et al. "Magnetic resonance imaging of the aqueous flow in eyes implanted with the trabeculo-suprachoroidal glaucoma seton" Invest. Ophthalmol. Vis. Sci. 33:948 (1992).

Lee KY. Trabeculo-suprachoroidal shunt for treating recalcitrant and secondary glaucoma. Presented at the American Academy of Ophthalmology Annual Meeting, Anaheim, CA, 1991.

Leske MC, Heijl A, Hussein M, et al for the Early Manifest Glaucoma Trial Group. Factors for glaucoma progression and the effect of treatment. The Early Manifest Glaucoma Trial. Arch Ophthalmol Jan. 2003;121:48-56.

Lichter PR, Musch DC, Gillespie BW, et al and the CIGTS Study Group. Interim clinical outcomes in the Collaborative Initial Glaucoma Treatment Study comparing initial treatment randomized to medications or surgery. Ophthalmology 2001;108:1943-53.

Losche W. "Proposals for improvement of cyclodialysis Klin Monatsblatter Augenheilkd Augenarztl Fortbild" 121(6):715-6 (1952) [German].

(56) References Cited

OTHER PUBLICATIONS

Marx et al., "Use of the Ganciclovir Implant in the Treatment of Recurrent Cytomegalovirus Retinitis" Arch Ophthal.; Jul. 1996; vol. 114:815-820.
McPherson "Combined Trabeculotomy and Cataract Extraction as a Single Operation" Tr. Am. Ophth. Soc., vol. LXXIV, 1976; 251-260.
Migdal C, Gregory W, Hitchings R. Long term functional outcome after early surgery compared with laser and medicine in open-angle glaucoma. Ophthalmology 1994;101:1651-7.
Miglior S, Pfeiffer N, Zeyen T et al for the European Glaucoma Prevention Study Group. Results of the European Glaucoma Prevention Study. Ophthalmology 2005;112:366-75.
Miglior S, Zeyen T, Pfeiffer N, et al for the European Glaucoma Prevention Study Group. The European Glaucoma Prevention Study design and baseline description of the participants. Ophthalmology 2002;109:1612-21.
Miki, MD et al., "Intraocular Cannula for Continuous, Chronic Drug Delivery-Histopathic Observations and Function" Arch Ophthal.; May 1985; vol. 103:712-717.
Molteno et al. "Long tube implants in the management of glaucoma" South African Medical Journal, Jun. 26, 1976;50(27):1062-6.
Molteno et al. "The Vicryl tie technique for inserting a draining implant in the treatment of secondary glaucoma." Australian and New Zealand Journal of Ophthalmology 1986; 14: 343-354.
Moses RA "Detachment of ciliary body-anatomical and physical considerations" Investigative Ophthalmology & Visual Science, Assoc. for Research in Vision and Ophthalmology, US, vol. 4, No. 5, Oct. 1, 1965.
Nesterov AP et al. "Surgical stimulation of the uveoscleral outflow. Experimental studies on enucleated human eyes" Acta Opthalmol (Copenh) June; 57(3):409-17 (1979).
Nguyen et al., "Complications of Baerveldt Glaucoma Drainage Implants" Arch Ophthal.; May 1998; vol. 116:571-575.
Noecker RJ. Clinical Evaluation of a Novel Gold Micro-Shunt for Reduction of 10 P in Refractory Glaucomas. American Glaucoma Society Annual Meeting, San Francisco, CA, 2007.http://www.glaucomaweb.org/associations/5224/files/AGS%20AM07%20Prgrm%20FINAL.pdf. Accessed Nov. 1, 2008).
O'Brien et al. "Cyclodialysis" Arch Ophthal. 1949;42(5):606-619.
Odrich. "The New Technique During Complex Tube-Shunt Implantation". *J. Glaucoma*. vol. 9 No. 3 (2000):278-279.
Olsen, Timothy W., et al., Cannulation of the Suprachoroidal Space: A Novel Drug Delivery Methodology to the Posterior Segment, American Journal of Ophthalmology, vol. 142, No. 5, Nov. 2006, pp. 777-787.e2.
Ozdamar et al. "Suprachoroidal seton implantation in refractory glaucoma: a novel surgical technique" J. Glaucoma Aug. 2003; 12(4):354-9.
Pinnas G. et al. "Cyclodialysis with teflon tube implants" Am J. Ophthalmol Nov. 1969; 68(5):879-883.
Portney GL, "Silicone elastomer implantation cyclodialysis." Arch Ophthalmol 1973; 89: 10-12.
Primary Open Angle Glaucoma. Preferred Practice Patterns, American Academy of Ophthalmology.http://one.aao.org/CE/PracticeGuidelines/PPP_Content.aspx?cid=a5a59e02-450b-4d50-8091-b2dd2lefl ff2#references (Accessed Nov. 1, 2008).
Pruett et al., "The Fishmouth Phenomenon-II. Wedge Scleral Buckling" Arch Ophthal.; Oct. 1977; vol. 95:1782-1787.
Qadeer "Acrylic Gonio-Subconjunctival Plates in Glaucoma Surgery " Br J Ophthalmol. Jun. 1954; 38(6): 353-356.
Quigley HA, Vitale S. Models of open-angle glaucoma prevalence and incidence in the United States. Invest Ophthalmol Vis Sci 1997; 38:83-91.
Richards et al. "Artificial Drainage Tubes for Glaucoma" Am J Ophth 60:1965,405-408.
Ritch, et al., "Uveoscleral Outflow", The Glaucomas. St. Louis: Mosby, 1996; pp. 337-343.
Rohen, Johannes W., Anatomy of the Aqueous Outflow Channels, Glaucoma, vol. 1, Chapter 14, pp. 277-296, Edited by J.E. Cairns, Grune & Stratton, Harcourt Brace Jovanovich Publishers, 1986.
Rosenberg, et al. "Implants in glaucoma surgery" Chapter 88, The Glaucomas, Ritch et al. Eds. 2nd Ed. Mosby St. Louis 1996; p. 1783-1807.
Row H. "Operation to control glaucoma: preliminary report" Arch. Ophthal 12:325 (1934).
Rowan, Patrick J., MD, Combined Cyclodialysis and Cataract Surgery, Ophthalmic Surgery and Lasers, Dec. 1998, vol. 29, No. 12, pp. 962-968 (9 pages).
Sampimon "A New Approach to Filtering Glaucoma Surgery" Ophthalmologica (Basel) 151: 1966, 637-644.
Schappert S. Office visits for glaucoma: United States, 1991-92. Advance data from vital and health statistics. vol. 262. Hyattsville, MD: National Center for Health Statistics, 1995.
Shaffer RN, Weiss DI. Concerning cyclodialysis and hypotony. Arch Ophthalmol 68: 25, 1962.
SOLX Clinical Literature Handout; Industry Show Feb. 2006; "The SOLX Gold Micro-shunt (GMS) treatment".
Sommer A, Tielsch JM, Katz J, et al. Racial differences in the cause-specific prevalence of blindness in east Baltimore. N Engl J Med 1991;325:1412-7.
Sourdille et al. "Reticulated hyaluronic acid implant in non-perforating trabecular surgery." J Cataract Refract Surg 25: 332-339. (1999):.
Spiegel et al. "Schlemm's Canal Implant: A New Method to Lower Intraocular Pressure in Patients With POAG?" *Ophthalmic Surgery and Lasers*. vol. 30, No. 6: 492-494. Jun. 1999.
Srinivasan et al. "Microbial contamination of the anterior chamber during phacoemulsification" J. Cataract Refract Surg. 28:2173-6 (2002).
Suguro K, Toris CB, Pederson JE. Uveoscleral outflow following cyclodialysis in the monkey eye using a fluorescent tracer. Invest Ophthalmol Vis Sci 1985: 26, 810.
The Advanced Glaucoma Intervention Study (AGIS): 7. The relationship between control of intraocular pressure and visual field deterioration. The AGIS Investigators. Am J Ophthalmol 2000;130:429-40.
The Advanced Glaucoma Intervention Study (AGIS); 13. Comparison of treatment outcomes within race: 10-year results. Ophthalmology 2004;111:651-64.
The Glaucoma Laser Trial (GLT) and Glaucoma Laser Trial Follow-up Study: 7. Results. Am J Ophthahnol 1995;120:718-31.
The Glaucoma Laser Trial (GLT). 2. Results of argon laser trabeculoplasty versus topical medicines. The Glaucoma Laser Trial Research Group. Ophthalmology 1990;97:1403-13.
Thiagalingam S, Tarongoy P, Hamrah P, Lobo AM, Nagao K, Barsam C, Bellows R, Pineda R. Complications of cosmetic iris implants. J Cataract Refract Surg. Jul. 2008:34(7)1222-4.
Tielsch JM, Sommer A, Katz J, et al. Racial variations in the prevalence of primary open-angle glaucoma. The Baltimore Eye Survey. JAMA 1991;266:369-74.
Toris CB. Extravascular albumin concentration of the uvea. Invest Ophthalmol Vis Sci 1990; 31:43.
Toris et al. "Aqueous humor dynamics in the aging human eye" Am J. Ophthalmol., 127:407-12 (1999).
Toris et al. "Effect of intraocular pressure on uveoscleral outflow following cyclodialysis in the monkey eye." Investigative Ophthalmology & Visual Science. 26 (1985) 1745-1749.
*Transcend Medical Inc. v. Glaukos Corporation*, Transcend Medical, Inc.'s Disclosures Pursuant to Default Discovery Rule 4 (d) (United States District Court for the District of Delaware, dated Dec. 6, 2013; case No. C.A. No. 13-830 (MSG) and Certificate of Service, dated Dec. 9, 2013.
Trigler L, Proia AD, Freedman SF. Fibrovascular ingrowth as a cause of Ahmed glaucoma valve failure in children. Am J Ophthalmol. Feb. 2006;141(2):388-9.
Troncoso Manuel U., "Cyclodialysis with insertion of metal implant in treatment of glaucoma, A Preliminary Report" Arch. Ophthal. 23:270 (1940).
Troncoso, Manuel U., Tantalum implants for inducing hypotny, Am Journal of Ophthalmology, vol. 32(4):499-508 (1949).

(56) References Cited

OTHER PUBLICATIONS

Van der Veen et al. "The gonioseton, a surgical treatment for chronic glaucoma. Documenta Ophthalmologica; vol. 75, Nos. 3-4, 365-375. (1990)".
Vossmerbaeumer U, Ditzen K, Jonas JB. Removal of an intracorneal hydrogel implant for hyperopia after LASIK. J Refract Surg. Jan. 2007;23(1):102-4.
Wagner, Justin A., et al., Characterization of Uveoscleral Outflow in Enucleated Porcine Eyes Perfused under Constant Pressure, Invest Ophthalmol Vis Sci., Published in edited form in Sep. 2004, vol. 45, Issue 9, pp. 3203-3206.
Wamsley S, Moster MR, Rai S, Alvim HS, Fontanarosa J. Results of the use of the Ex-Press miniature glaucoma implant in technically challenging, advanced glaucoma cases: a clinical pilot study. Am J Ophthalmol. Dec. 2004; 138(6): 1049-51.
Yablonski, "Some thoughts on the pressure dependence of uveoscleral flow" Journal of Glaucoma, 12(1):90-92 (2003).
Yablonski, "Trabeculectomy with Internal Tube Shunt: a novel glaucoma surgery" J. Glaucoma 14:91-97 (2005).
Yoo C, Kwon SW, Kim YY. Pericardium plug in the repair of the corneoscleral fistula after ahmed glaucoma valve explantation. Korean J Ophthalmol. Dec. 2008;22(4):268-71.
Zhou et al. "A trabecular bypass flow hypothesis" J Glaucoma. 14(1):74-83 (2005).
In the Commonwealth of Australia—In the Matter of Australian Patent Application No. 2006336598 in the name of Transcend Medical, Inc. ("Applicant") and Opposition thereto by Glaukos Corporation ("Opponent"), Commonwealth of Australia—Opponent's Statement of Grounds and Particulars of Opposition. (Apr. 10, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Mr. Craig Andrews in support of Opponent's opposition. (Sep. 9, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Colin Clement in support of Opponent's opposition. (Sep. 9, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Ilesh Patel in support of Opponent's opposition. (Sep. 9, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Opponent's amended Statement of Grounds and Particulars of Opposition. (Sep. 10, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Robert L. Stamper in support of Applicant's Evidence in Answer. (Dec. 4, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Jonathan G. Crowston in support of Applicant's Evidence in Answer. (Dec. 6, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Anne Jen-Wan Lee in support of Applicant's Evidence in Answer. (Dec. 7, 2014).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Colin Clement in support of Opponent's Evidence in Reply. (Feb. 8, 2015).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Ilesh Patel in support of Opponent's Evidence in Reply. (Feb. 10, 2015).
In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Mr. Craig Andrews in support of Opponent's Evidence in Reply. (Feb. 11, 2015).
Schocket, Stanley S. "Investigations of the Reasons for Success and Failure in the Anterior Shunt-to-the-Encircling-Band Procedure in the Treatment of Refractory Glaucoma." Tr. Am. Ophth. Soc.vol. LXXXIX. (1986):743-798.

\* cited by examiner

FLOW PROMOTING OCULAR IMPLANT

REFERENCE TO PRIORITY DOCUMENT

This application claims the benefit of priority under 35 U.S.C. §119(e) of U.S. Provisional Patent Application Ser. No. 61/726,477 filed Nov. 14, 2012 under 37 C.F.R. §1.76 (a). Priority of the filing date is hereby claimed and the full disclosure of the aforementioned application is incorporated herein by reference.

BACKGROUND

The mechanisms that cause glaucoma are not completely known, though glaucoma has been linked to abnormally high pressure in the eye, which can lead to optic nerve damage. Over time, the increased pressure can cause damage to the optic nerve, which can lead to blindness. Treatment strategies have focused on keeping the intraocular pressure down in order to preserve as much vision as possible over the remainder of the patient's life.

Pursuant to such strategies, one or more implants can be delivered into the eye for shunting fluid out of the anterior chamber in order to regulate pressure in the eye. Accurate placement of an implant in the angle of the eye can be critical for the targeted effect of reducing intraocular pressure (IOP). Placing an implant too distally into the eye, such as too distally into the supraciliary space, may leave no portion of the implant remaining in the anterior chamber. This can inhibit aqueous outflow, as the fluid will not have a direct communication with the flow target location if there is no opening to the anterior chamber.

Conversely if the implant is placed too proximally in the supraciliary space such that a significant portion of the implant remains in the anterior chamber, damage to the corneal endothelium may result from implants that protrude upwards and touch the cornea. Implants placed too proximally may also touch the iris resulting in increased amounts of pigment dispersion in the eye, which can increase outflow resistance and intraocular pressure by clogging the trabecular meshwork. Therefore, correct placement of the implant is desired for a safe and a successful surgical outcome.

Additionally, in at least some instances, reduction in IOP can be correlated with forming one or more areas of separation between parts of the eye, such as between the choroid and sclera. These areas of separation can at least assist in allowing fluid to flow from the anterior chamber of the eye to the suprachoroidal space or supraciliary space. However, although creating separation between parts of the eye may be beneficial, creating larger incisions in the eye is generally not. For instance, a larger diameter implant may be able to create greater separation between parts of the eye, such as between the sclera and choroid, but a larger incision would be necessary which can result in excess tissue damage to the eye.

SUMMARY

Disclosed herein are devices and methods related to implants for treating one or more physiological conditions of the eye. Some device embodiments disclosed herein include an ocular implant for implanting in an eye, which can include an elongate tubular body comprising a proximal end, a distal end and an inner lumen extending at least partway between the proximal end and the distal end. In addition, the ocular implant can include a fenestration extending from an outer surface of the tubular body and intersecting with the inner lumen, and an extruded feature extending from the outer surface of the tubular body and positioned adjacent the fenestration.

Some system embodiments disclosed herein include an implant delivery system including an implant configured for implantation into an eye where the implant can have an elongate tubular body including a proximal end, a distal end and an inner lumen extending at least partway between the proximal end and the distal end. In addition, the implant can include a fenestration extending from an outer surface of the tubular body and intersecting with the inner lumen, and an extruded feature extending from the outer surface of the tubular body and positioned adjacent the fenestration. Additionally, the delivery system can include a delivery device configured to insert the implant into the eye.

Some method embodiments disclosed herein include implanting an implant in an eye, with the method including securing an implant to a delivery device configured to insert the implant into the eye. In addition, the implant can include an elongate tubular body including a proximal end, a distal end and an inner lumen extending at least partway between the proximal end and the distal end. Additionally, the implant can include a fenestration extending from an outer surface of the tubular body and intersecting with the inner lumen, and an extruded feature extending from the outer surface of the tubular body and positioned adjacent the fenestration. The method can further include inserting the implant into the eye.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

This disclosure describes methods and devices related to implanting an ocular implant into an eye for promoting fluid flow within the eye in order to treat a variety of diseases and ailments of the eye, including open angle glaucoma and narrow angle glaucoma. Some device embodiments described herein include ocular implants which are compact enough such that they do not require a large incision for implantation but can provide improved separation between one or more parts of the eye, such as between the sclera and choroid.

At least some embodiments of the ocular implant disclosed herein are configured to assist in promoting fluid flow from the anterior chamber of the eye to either the suprachoroidal space or the supraciliary space. In addition, the ocular implants can include a variety of features, including extruded features and fenestrations, which can assist in promoting fluid flow at least through the implant.

Figure 1:
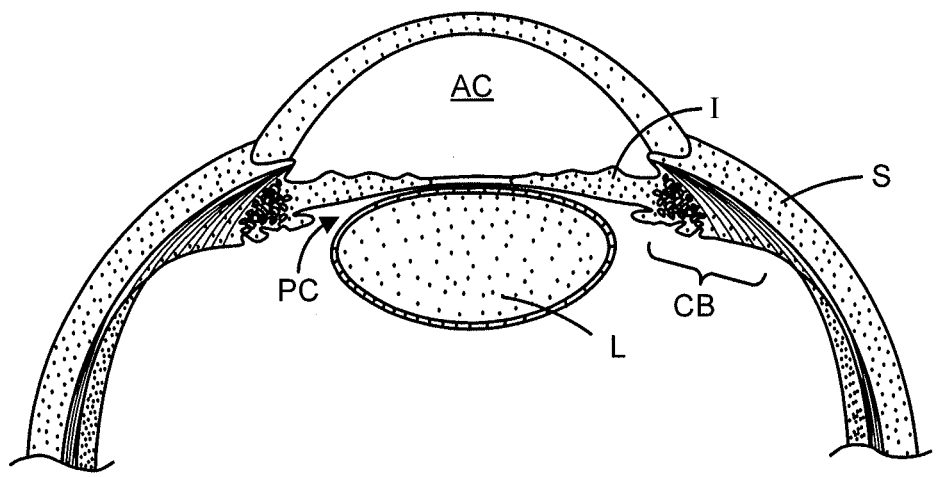
FIG. 1 shows an example cross-sectional view of a portion of the human eye.

FIG. 1 is a cross-sectional view of a portion of the human eye. The eye is generally spherical and is covered on the outside by the sclera S. The retina lines the inside posterior half of the eye. The retina registers the light and sends signals to the brain via the optic nerve. The bulk of the eye is filled and supported by the vitreous body, a clear, jelly-like substance. The elastic lens L is located near the front of the eye. The lens L provides adjustment of focus and is suspended within a capsular bag from the ciliary body CB, which contains the muscles that change the focal length of the lens. A volume in front of the lens L is divided into two by the iris I, which controls the aperture of the lens and the amount of light striking the retina. The pupil is a hole in the center of the iris through which light passes. The volume between the iris and the lens is the posterior chamber PC. The volume between the iris and the cornea is the anterior chamber AC. Both chambers are filled with a clear liquid known as aqueous humor.

The ciliary body continuously forms aqueous humor in the posterior chamber by secretion from the blood vessels. The aqueous humor flows around the lens and iris into the anterior chamber and exits the eye through the trabecular meshwork, a sieve-like structure situated at the corner of the iris and the wall of the eye (the corner is known as the iridocorneal angle or the angle). Some of the aqueous humor can filter through the trabecular meshwork near the iris root into Schlemm's canal, a small channel that drains into the ocular veins. A smaller portion rejoins the venous circulation after passing through the ciliary body and eventually through the sclera (i.e., the uveoscleral route).

Figure 2:
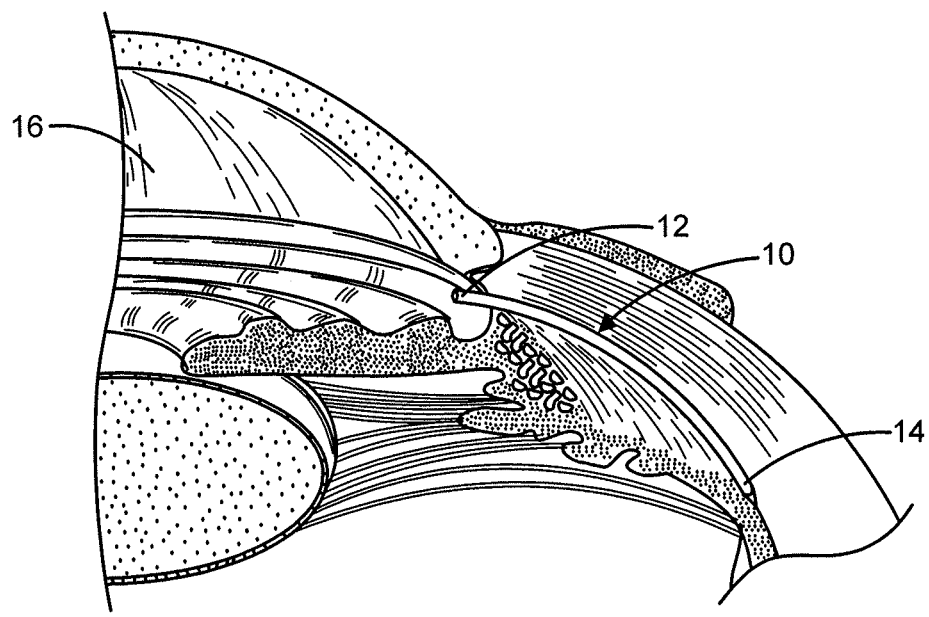
FIG. 2 shows and an example cross-sectional perspective view of a portion of the eye showing a part of the anterior and posterior chambers of the eye and a schematic representation of an embodiment of an implant positioned inside the eye such that a proximal end is located in the anterior chamber and a distal end communicates with and/or is located in or near the supraciliary space.

FIG. 2 is a cross-sectional, perspective view of a portion of the eye showing the anterior and posterior chambers of the eye. A schematic representation of an embodiment of an implant 10 is shown positioned inside the eye such that a proximal end 12 is located in the anterior chamber and a distal end 14 communicates with and/or is located in or near the supraciliary space. In another embodiment, the distal end 14 is located in the suprachoroidal space. It should be appreciated that FIG. 1 and other figures herein are schematic and are not necessarily to scale with respect to size and relative positions of actual eye tissue.

The ocular implants disclosed herein can provide a fluid pathway between at least the anterior chamber and either the supraciliary space or suprachoroidal space. For example, the implant can include a distal end that can be positioned in the supraciliary space or the suprachoroidal space. The implant may be positioned at least partially between the ciliary body and the sclera or it may be at least partially positioned between the sclera and the choroid. The distal end of the implant may be positioned between other anatomical parts of the eye.

In some embodiments, the implant can include an elongated tubular body having one or more internal lumens through which aqueous humor can flow, such as from the anterior chamber into either the suprachoroidal or supraciliary space. The implant can have a substantially uniform internal diameter along its entire length, although the shape of the implant can vary, such as along its length. Alternatively, the implant can have a variable internal diameter along its length. Moreover, the implant can have various cross-sectional shapes, such as a circular, oval or rectangular shape, and can vary in cross-sectional shape moving along its length. For example, the cross-sectional shape can be selected to facilitate easy insertion into the eye.

The internal lumen of the implant can serve as a passageway for the flow of aqueous humor through the implant directly from the anterior chamber toward or into the suprachoroidal space or supraciliary space. In addition, the internal lumen of the implant can be used as an access location to mount the implant onto a delivery system. The internal lumen can also be used as a pathway for flowing fluid, such as an irrigation fluid or a visco-elastic substance, into the eye for flushing or to maintain pressure in the anterior chamber, or using the fluid to assist in dissection, visualization or hydraulic creation of a dissection plane into or within the supraciliary or suprachoroidal space. Fluid can be flowed toward or into either the supraciliary or suprachoroidal space, for example via a delivery cannula or through the internal lumen of the shunt. The fluid can be flowed into the eye with a pressure sufficient to form a dissection plane into or within the supraciliary or suprachoroidal space. The fluid can accumulate within the eye so as to form a lake. In general, hydro-dissection or the injection of fluids such as visco-elastic substances can be used to separate the ciliary body from the sclera to enlarge an area of detachment of the ciliary body from the sclera with or without insertion of a device.

In at least some instances reduction in IOP can be correlated with the position of the implant which creates an area of separation between the choroid and sclera around at least a part of the implant (also known as "tenting") and a space created around, for example, the most distal portion of the implant (also known as an "aqueous lake"). In addition, increasing the area of scleral and choroidal separation can improve IOP reduction in at least some instances.

Although increasing the area of scleral and choroidal separation can be advantageous, several drawbacks can occur if a lager implant, such as an implant larger than approximately 0.5-1.0 mm in diameter, is used to create the larger separation. For example, some drawbacks may include the requirement for a larger incision, such as along the limbus, due to a greater diameter implant. A larger incision may cause fluids to escape the eye, such as at least from the anterior chamber, and complicate the implantation procedure. For example, an incision less than 2.5 mm may be preferable for implantation of at least one implant.

Other drawbacks to using a larger diameter implant can include creating a larger cyclodialysis which may result in increased rates of hypotony post operatively and increased rates of retinal detachments. In addition, a larger implant can be more difficult to insert into the supraciliary and suprachoroidal space due to the requirement of greater tissue separation which may result in excess tissue damage. Therefore, an implant which is sized such that it does not require a large incision (such as less than 2.5 mm) and can promote the flow of aqueous fluid from the anterior chamber of the eye to the suprachoroidal space or supraciliary space may overcome the drawbacks discussed above while achieving an improved reduction in IOP.

The present disclosure includes various embodiments of ocular implants, such as implants which include a tubular structure having at least one inner lumen which extends through the length of the implant. For example, the proximal end can be configured to be positioned in the eye such that it allows aqueous fluid to flow into the inner lumen of the implant. The distal end of the implant can be configured and positioned in the eye such that it allows aqueous fluid to flow out of the implant. In addition, the proximal and distal end of the implant can include features that assist in promoting fluid flow through the implant and protect the eye from damage.

Additionally, either the proximal end or distal end of the implant can be radiused or chamfered in order to protect the eye from damage, such as from sharp edges. For example, at least one of the distal end and proximal end of the implant can be radiused or chamfered for promoting smooth insertion and interaction with surrounding tissue which can assist in minimizing cyclodialysis. Alternatively or in addition, either the proximal end or distal end of the implant can include features which assist in preserving or promoting fluid flow through the implant. For example, the proximal end or distal end can include a beveled or wave cut tip which can assist in preventing at least surrounding tissue from occluding the inner lumen and preventing fluid flow through the implant. Any number of a variety of proximal end or distal end shapes can be included in an implant implementation for assisting in preserving or promoting fluid flow through the implant.

Some implementations of the implant can include at least one fenestration. Any one fenestration can be placed anywhere along the implant, including at the proximal end, distal end, or along the length of the implant, for assisting in fluid flow through the implant. In addition, the fenestrations can have any number of a variety of sizes and shapes and can be arranged in any number of a variety of patterns along the implant. For example, the size of the fenestrations can increase distally which can assist in promoting fluid flow in the distal direction relative to the implant. Alternatively or in addition, the number of fenestrations can increase in the distal direction along the length of the implant, such that there are more fenestrations adjacent the distal end, which can also assist in promoting distal fluid flow.

Furthermore, one or more fenestrations can be in the shape of a channel which can extend along the length of the implant. More than one channel can extend along the distal end of the implant and form, for example, a bifurcated or trifurcated configuration. In addition, the channels can widen in the distal direction along the implant. Any of a variety of sized and shaped fenestrations positioned at one or more locations along the implant can assist in creating a pressure gradient which can promote distally directed flow in order to increase fluid flow through the implant in the distal direction and reduce IOP.

Some implementations of the implant can include one or more extruded features, such as for assisting fluid flow into one or more fenestrations. For example, one or more extruded pegs or rings can be positioned adjacent or near one or more fenestrations, including the main inlet and outlet port of the implant. The extruded features, such as the extruded pegs or rings, can assist in preventing surrounding tissue from blocking or occluding the fenestrations which can allow the implant to efficiently and effectively promote fluid flow through the implant and reduce IOP.

Alternatively or in addition, one or more features can be indented into the body of the implant for assisting with fluid flow through the implant. Any number of a variety of shaped and sized features, both indented and extruded, can be included in an implant for assisting with fluid flow through the implant, such as by preventing at least surrounding tissue from blocking or occluding one or more fenestrations.

In some embodiments, the implant can include a lumen which is partially or completely occluded with a bioasbsorbable material. The bioasborbable material can be comprised of, for example, a polylactic acid (PLA), polylactic-co-glycolic acid (PLGA), any combination of these materials, or any other suitable degradable material. The bioabsorbable material can be configured to block the flow of fluid through the lumen during a post-operative period, such as, for example, the first week, first several weeks or first several months after implantation. The bioabsorbable material can assist in preventing tissue growth in the lumen of the implant during the post-operative period when foreign body reaction and inflammation may be highest. After a period of time, the bioabsorbable material may erode away and the lumen of the implant may become patent and allow fluid to flow through the lumen.

In some embodiments, the bioabsorbable material can be molded onto either end of the implant, such as like a cap. Alternatively, the bioabsorbable material may be filled through the entire lumen of the implant at a temperature above the melting temperature of the bioabsorbable material and then allowed to cool and form within the lumen. In addition, the bioabsorbable material may fill through any number of channels or cavities within the implant.

In addition, some extruded features, such as extruded pegs or rings, can assist in maintaining the implant in a desired location within the eye. For example, at least one extruded ring can be positioned along the length of the implant, such as at either the proximal or distal end of the implant, which can assist in retaining the implant in a desired location. By preventing migration of the implant after implantation in the eye, the implant can be prevented from causing damage to the eye and can work efficiently and effectively to reduce IOP.

Additionally, any one or more extruded feature can assist in providing tenting around one or more parts of the implant, including around at least one fenestration. The size, shape and positioning relative to one or more fenestrations (e.g., adjacent to one or more fenestrations) can affect the tenting effect and resulting fluid flow through the implant. Therefore, the extruded features can include any number of a variety of sizes, shapes and positions along the implant in order to achieve desired tenting effects and fluid flow through the implant.

Furthermore, some extruded features can be sized, shaped and positioned along the implant in order to assist in positioning the implant in the eye. For example, an extruded feature can include a larger diameter proximal extruded ring which can provide a hard stop during implantation. This can assist a user, such as a clinician, in determining the proper positioning of the implant and can assist in preventing over-insertion of the implant.

The implant can be made out of any number of medical grade materials, including at least one of stainless steel, polyimide, or other plastics and metal materials. Alternatively or in addition, the implant can be made out of any number of shape memory alloys, such as nitinol, or shape memory polymers. However, any number of medical grade materials may be used.

In addition, the implant can be coated with a drug, such as mitomycin or 5-FU which can be used, for example, in trabeculectomy surgeries in order to reduce fibrotic and inflammatory tissue response. One or more drugs can be adhered to the surface of the implant. Alternatively or in addition, the one or more drugs may be combined with a polymer comprising at least a part of the implant for a sustained release profile.

Figure 3A:
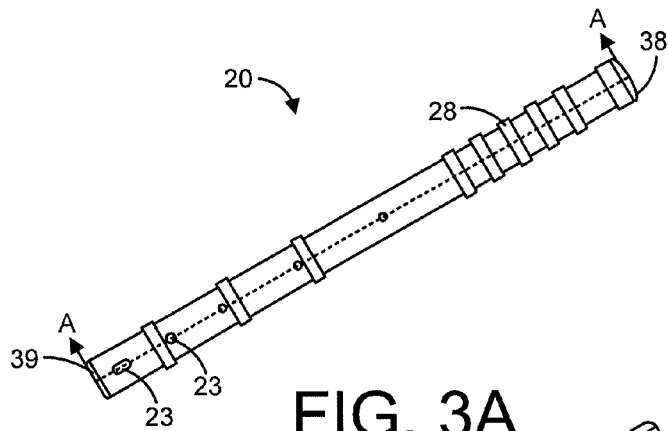
FIG. 3A illustrates a side view of an embodiment of an ocular implant having a tubular body with an inner lumen and at least one fenestration.
Figure 3B:
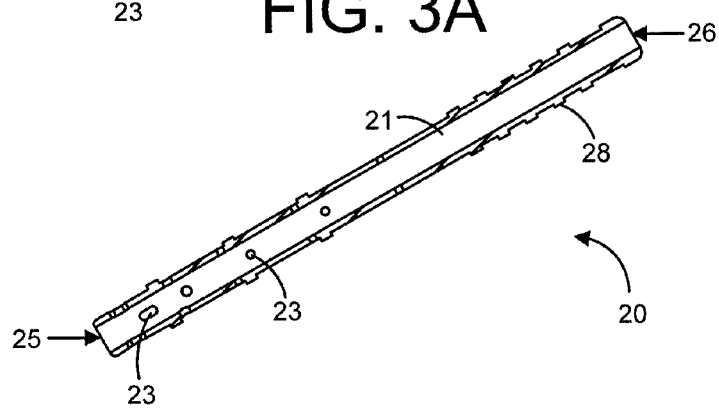
FIG. 3B illustrates a cross-section view of the implant in FIG. 3A showing the fenestrations in fluid communication with the inner lumen.

FIGS. 3A and 3B illustrate an embodiment of an ocular implant 20 having a tubular body with an inner lumen 21 which can extend through the length of the implant 20. In addition, the implant 20 can include at least one fenestration 23 along the length of the implant 20. The fenestrations 23 can provide a fluid passageway between one or more areas surrounding the implant 20 and the inner lumen 21 of the implant 20. Additionally, the fenestrations 23 can assist in promoting fluid flow through the implant 20, such as aqueous fluid, in order to reduce IOP.

For example, the fenestrations 23 can provide additional fluid passageways through the implant 20 other than though a main outlet port 25 at the distal end of the implant 20 or a main inlet port 26 at the proximal end of the implant 20. In addition, in the event either the main outlet port 25 or the main inlet port 26 of the implant 20 is occluded, the fenestrations 23 can provide alternate fluid passageways for fluid flowing through the implant 20, such as aqueous fluid flowing from the anterior chamber into the suprachoroidal space or supraciliary space.

Any number of fenestrations 23, which can vary in shape and size, can be positioned anywhere along the length of the implant 20. Additionally, the density of fenestrations 23 along the length of the implant 20 can vary. For example, more fenestrations 23 may be positioned near the distal end of the implant 20 than near the proximal end. As shown in FIGS. 3A and 3B, the number of fenestrations can increase distally along the implant 20. By increasing the number of fenestrations 23 along the implant 20 in the distal direction, distally directed fluid flow through the implant 20 can be promoted, such as by the formation of a pressure gradient. For example, this can be beneficial when the proximal end of the implant is positioned in the anterior chamber and the distal end is positioned in the suprachoroidal or supraciliary space for treatment of an eye having high IOP.

Additionally, as shown in FIGS. 3A and 3B, the fenestrations 23 can increase in size along the length of the implant 20. More specifically, the fenestrations 23 can increase in diameter as they are positioned closer to the distal end of the implant 20. Increasing the size of the fenestrations 23 in the distal direction along the length of the implant 20 can assist in creating a pressure gradient, which can promote distally directed flow. The implant 20 can have any number of a variety of sized and shaped fenestrations along the length of the implant 20 that can assist in promoting fluid flow through the implant 20, including promoting a distally directed fluid flow.

Therefore, by either increasing the number of fenestrations or the size of the fenestrations along a length of the implant in the distal direction, distally directed flow can be promoted through the implant 20 without having to increase either the inner diameter or outer diameter of the implant 20. This can allow the implant 20 to maintain a smaller diameter, which can be beneficial at least during implantation, while providing one or more fluid passageways that aggregately provide improved fluid flow between at least the proximal end and distal end of the implant.

In addition, FIGS. 3A and 3B illustrate an ocular implant 20 having one or more extruded features configured as rings 28 extending from the outer surface of the implant 20. The rings 28 can provide additional separation between the tissue surrounding the implant 20, such as the choroid and sclera. The rings 28 can assist in creating additional space, also known as tenting, which can promote fluid flow through the implant and reduce IOP without requiring the entire length of the implant 20 to increase in diameter. The tenting effect provided by the rings 28 can assist in preventing surrounding tissue from occluding the fenestrations 23. Occlusion of the fenestrations can reduce fluid flow through the implant 20 which can hinder the implant 20 from assisting with reducing IOP. For example, the one or more extruded features can improve fluid flow, such as by tenting, and minimize the potential for sclera or choroidal occlusion of the fenestrations 23 which can more effectively reduce IOP.

In some implementations, one or more rings 28 can be positioned at or near the distal end of the implant 20 for assisting in preventing occlusion of the more distally positioned fenestrations 23. In addition, one or more rings 28 can be positioned at or near the proximal end of the implant 20 for assisting in preventing occlusion and providing additional retention. Extruded features, such as rings 28, positioned along the implant 20, both proximally and distally, can provide additional retention of the implant 20 which can ensure against migration of the implant 20 after implantation. The size and shape of the rings 28 may vary and any number of rings 28 can extend along the length of an implant 20.

Figure 4A:
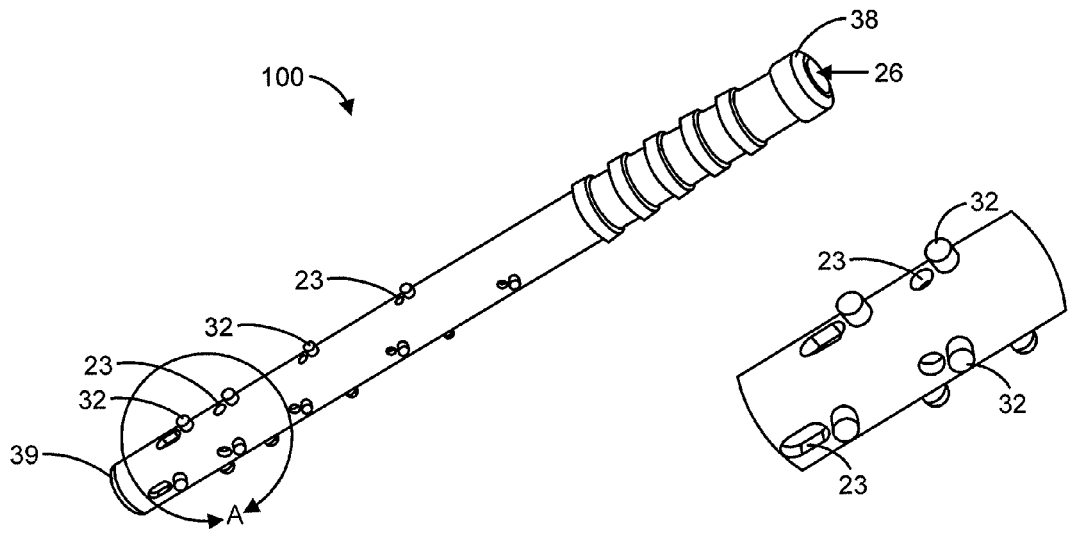
FIG. 4A illustrates an embodiment of an implant having a variety of shaped and sized extruded features, including extruded rings and pegs.
Figure 4B:
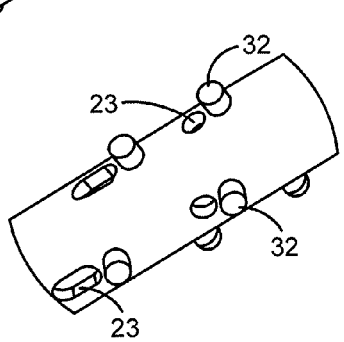
FIG. 4B shows an enlarged section view of the implant in FIG. 4A showing the position of the pegs adjacent fenestrations for assisting in preventing occlusion of the fenestrations.

FIGS. 4A and 4B illustrate an embodiment of an implant 100 having a variety of shaped and sized extruded features. The implant 100 includes at least one ring 28 along the length of the implant, such as near the proximal end for at least providing retention of the implant 20 in the eye after implantation. In addition, the implant 100 includes at least one peg 32 along the length of the implant 20, such as near the distal end of the implant for at least assisting in efficient fluid flow through the implant 100 (i.e., by assisting in creating either a tenting effect or an aqueous lake). As with any extruded feature, the pegs 32 can vary in size and shape, including along the length of the implant 100.

FIG. 4A shows the pegs 32 increasing in diameter in the distal direction along the length of the implant 100. This configuration can assist in providing an increase in either tenting or aqueous lake effects, which can assist in promoting distally directed flow through the implant 100. The fenestrations 23 positioned along the implant 100 are also shown as distally increasing in diameter along the length of the implant which can also assist in promoting distally directed fluid flow through the implant 100, such as by creating a pressure gradient.

As shown in FIG. 4B, the extruded features, such as the pegs 32, can be positioned directly adjacent fenestrations 23 which can allow the extruded features to assist in preventing occlusion of the fenestrations 23 by pushing surrounding tissue away from the fenestrations 23. In addition, the extruded features, such as the pegs 32, can vary in height in order to provide a variety of tenting effects. Additionally, any number of a variety of features can be included to assist in creating a tenting effect, such as a sheath or cage which can expand around the fenestrations, without departing from the scope of this disclosure.

Figure 5:
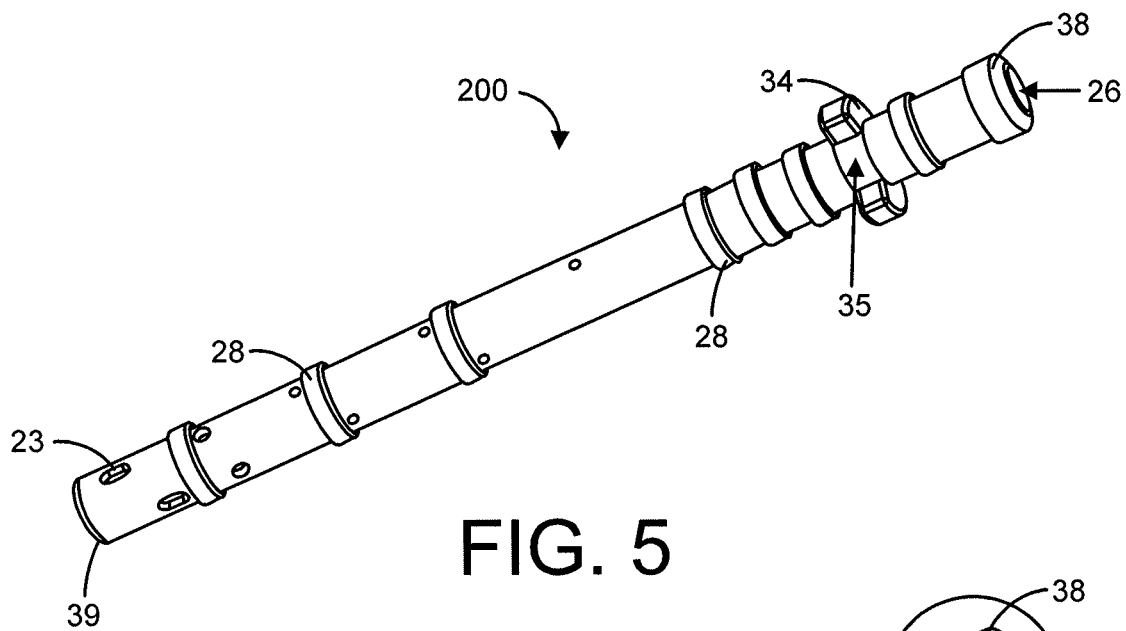
FIG. 5 illustrates an embodiment of an implant having an extruded feature configured as a large proximal ring.

FIG. 5 illustrates an embodiment of an implant 200 having an extruded feature configured as a large proximal ring 34. The large proximal ring 34 can be a large extruded feature, such as a ring, and positioned proximally in order to assist a user, such as a clinician, with properly inserting the implant 200. For example, the large proximal ring 34 can be used as a reference hard stop for placement of the implant 200 which can assist in preventing over-insertion of the implant 200. Improperly placed implants can at least cause either damage to the eye or prevent the implant from performing efficiently and effectively. Therefore, the large proximal ring 34 can be beneficial in assisting a clinician with properly placing the implant 200 for allowing the implant 200 to efficiently and effectively reduce IOP without causing significant damage to the eye.

As shown in FIG. 5, the large proximal ring 34 can include at least one cutout 35. The cutout 35 can be oriented to face the iris when the implant 200 is implanted in the eye. This can allow the cutout 35 to at least minimize contact between the implant 200, such as the large ring 34, and the iris. In addition, the implant 200 can also include one or more extruded features, such as rings 28, and fenestrations 23 for at least assisting in promoting fluid flow through the implant, including distally directed fluid flow.

Figure 6A:
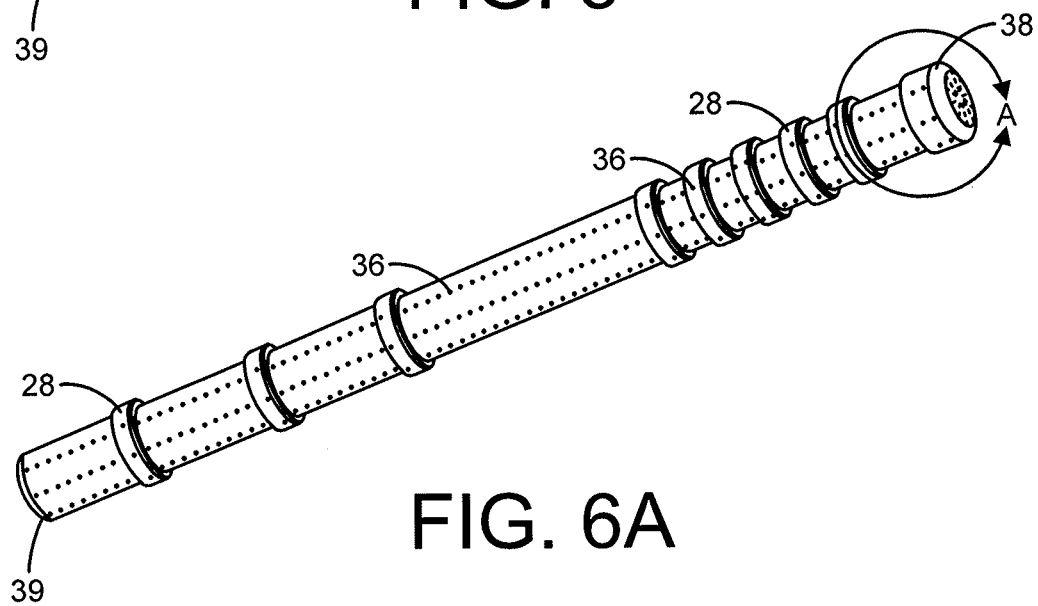
FIG. 6A illustrates an embodiment of an implant having a plurality of micro-channels.
Figure 6B:
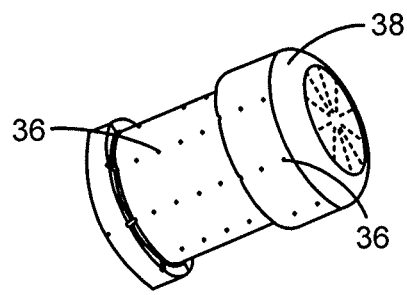
FIG. 6B shows an enlarged section view of the implant in FIG. 6A showing a proximal end of the implant which can have one or more fenestrations or micro-channels extending through a proximal outer wall of the implant.

FIGS. 6A and 6B illustrate an embodiment of an implant 300 having a multitude of micro-channels 36. The micro-channels 36 can have a small diameter, such as no greater than microns, and can provide a mechanism for allowing fluid transport through the implant 300. The micro-channels 36 can run either axially along the length of the implant or radially along the length of the implant 300 which can form a meshwork of micro-channels 36. In some embodiments, the micro-channels 36 which make up the meshwork of micro-channels 36 can vary in size and shape.

In some embodiments, micro-channels 36 can be sized and configured such that they restrict fluid flow through the micro-channels 36 similar to a valve. For example, when the pressure in the anterior chamber drops below 12 mmHg the micro-channels 36 can at least reduce the amount of fluid flow through the micro-channel lumens, including preventing fluid flow altogether. By at least reducing the amount of fluid flow through the micro-channels 36 when pressure drops in the anterior chamber, the implant 300 can assist in preventing the eye from becoming hypotonous. By way of further example, when the pressure in the anterior chamber is above 12 mmHg, fluid can be allowed to flow through the micro-channels 36, such as to assist in reducing IOP.

The micro-channels 36 can increase in size from the proximal end to the distal end of the implant 300, which can assist in promoting distally directed fluid flow. Alternatively or in addition, one or more fenestrations 28 or micro-channels 36 that are larger in diameter can be placed at or near the middle portion of the implant 300 where an increase in tenting can occur.

In some embodiments, the micro-channels 36 or fenestrations 28 of the implant 300 can either form or intercept a bifurcated or trifurcated configuration at the distal end of the implant 300. The bifurcated or trifurcated configuration at the distal end of the implant 300 can assist in reducing pressure at the bifurcated or trifurcated locations and promote distally directed flow through the implant 300. Any number of fenestration 28 or micro-channel configurations can be implemented in an implant without departing from the scope of this disclosure.

FIG. 6B shows the proximal end of the implant 300 which can have one or more fenestrations 28 or micro-channels 36 extending through a proximal outer wall of the implant 300. The implant 300 can also include a distal outer wall having either one or more fenestrations 28 or micro-channels 36 extending therethrough.

As shown in at least FIGS. 3A-6B, at least one of the proximal end and distal end of the implant can have either a radiused edge 38 or chamfered edge 39. The radiused edges 38 and chamfered edges 39 can assist in inserting the implants into the eye and preventing damage to the at least during and after implantation of the implant in the eye. Any one implant can include any one of a variety of shaped and sized radiused edge 38 or chamfered edge 39, including along any extruded feature, proximal end or distal end, for at least assisting with implanting the implant and preventing damage to the eye without departing from the scope of this disclosure.

Figure 7A:
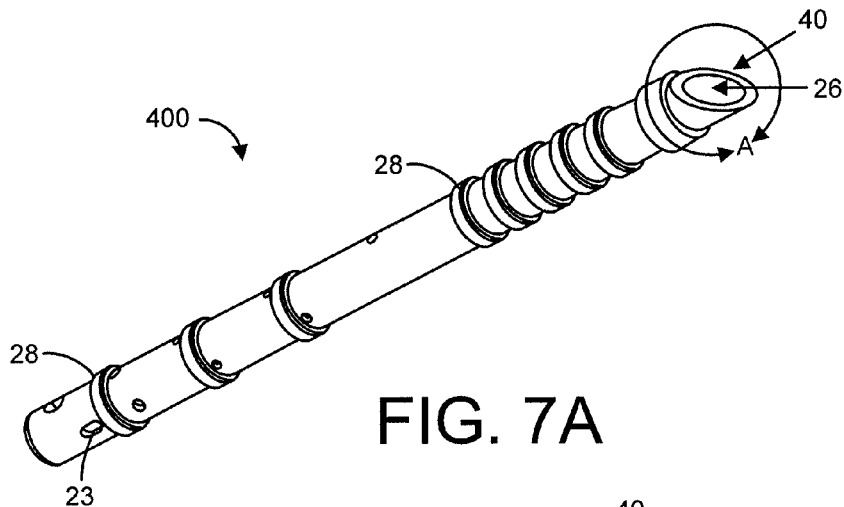
FIG. 7A illustrates an embodiment of an implant having a beveled proximal end.
Figure 7B:
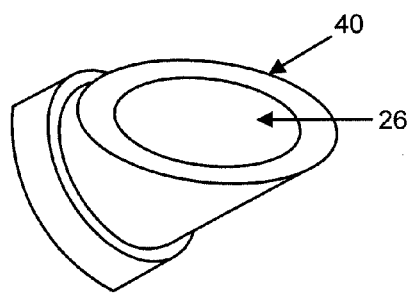
FIG. 7B shows an enlarged section view of the implant in FIG. 7A showing the beveled proximal end and a main inlet port.

FIGS. 7A and 7B illustrate an embodiment of an implant 400 having a beveled 40 proximal end. The bevel 40 can be oriented such that the elliptical face of the bevel 40 can face away from the iris in order to at least minimize occlusion of the main inlet port 26, such as by the iris. The beveled 40 proximal end can also include at least one micro-channel 36 or fenestration 28 similar to the embodiment described in FIGS. 6A and 6B. In addition, although shown as having only a beveled 40 proximal end, any one implant can have either a beveled 40 proximal end or a beveled 40 distal end.

Figures 8A, 8B:
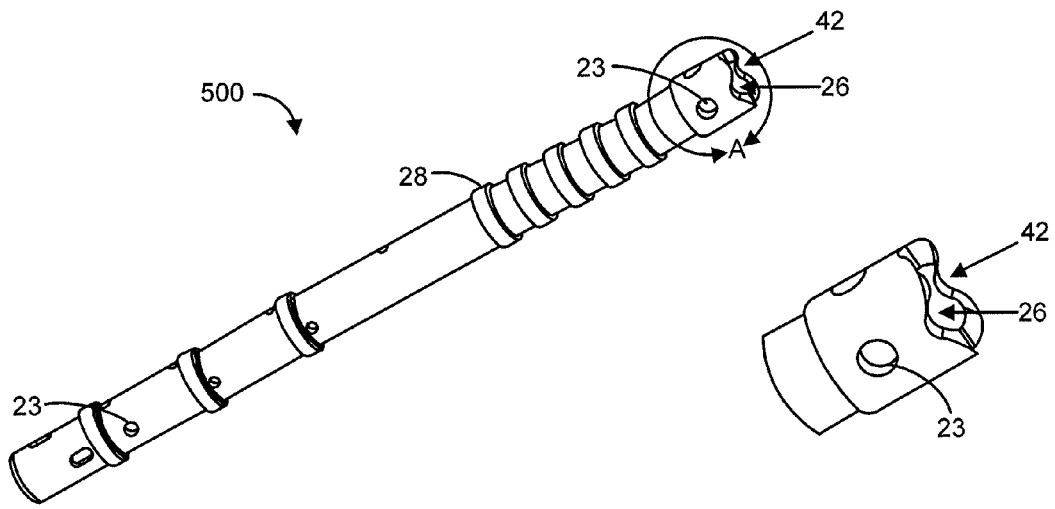
FIG. 8A illustrates an embodiment of an implant having a wave-cut proximal end including at least one fenestration adjacent the proximal end of the implant.
FIG. 8B shows an enlarged section view of the implant in FIG. 7A showing the wave-cut proximal end with at least one fenestration adjacent the proximal end of the implant.

FIGS. 8A and 8B illustrate an embodiment of an implant 500 having a wave-cut 42 proximal end including at least one fenestration 28 adjacent the proximal end of the implant 500. At least one of the wave-cut 42 proximal end and fenestrations 28 can assist in preventing occlusion of the proximal end of the implant 500, such as by the iris or surrounding tissue. Additionally, the fenestrations 28 adjacent the proximal end of the implant 500 can provide another inlet for aqueous fluid to enter the implant 500, such as in the event the main inlet port 26 is occluded. The wave-cut 42 proximal end and proximal fenestrations 28 can be included in any implant embodiment for at least assisting in fluid flow through the proximal end of the implant.

Figure 9:
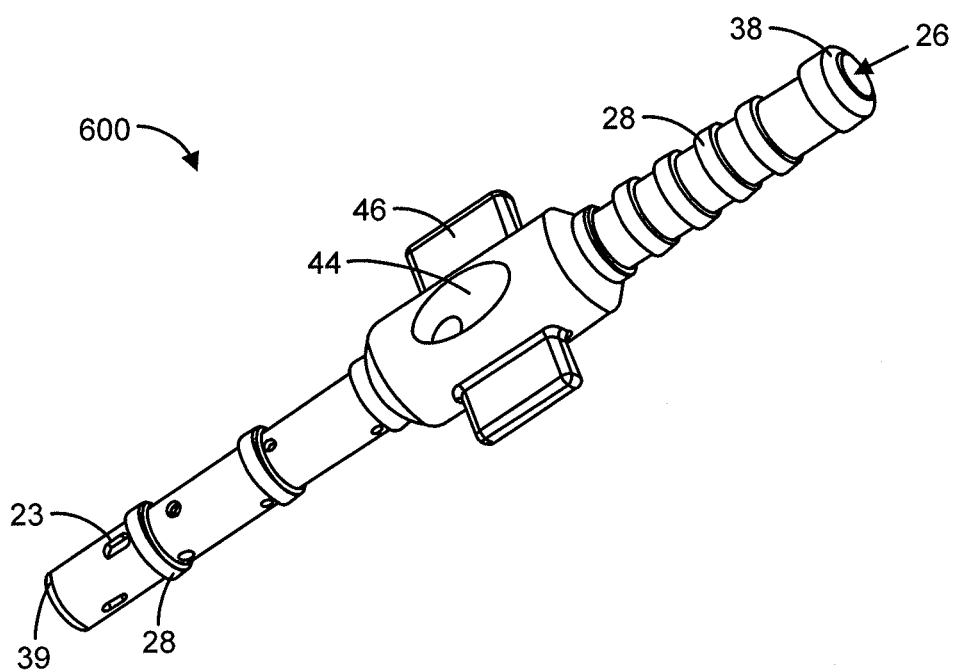
FIG. 9 illustrates an embodiment of an implant including stabilizing features and a receiving port for receiving one or more drugs.

FIG. 9 illustrates an embodiment of an implant 600 including a receiving port 44 for receiving one or more drugs, such as drugs for reducing fibrotic and inflammatory tissue response. For example, the one or more drugs can be released by the implant 600 into the eye, such as during and after implantation of the implant 600 in the eye. The receiving port 44 can be positioned anywhere along the implant 600, including the middle portion, as shown in FIG. 9. The position of the receiving port 44 along the implant 600 can depend on a number of factors, including where the one or more drugs received by the receiving port 44 are to be dispensed from the implant 600. In addition, the position of the receiving port 44 along the implant 600 can depend on the availability of the receiving port 44 to be accessed by a clinician either during or after implantation of the implant 600 for delivering one or more drugs to the receiving port 44. It can be beneficial to position the receiving port 44 along the implant 600 in order to allow a needle to locate the receiving port 44 and properly deliver one or more drugs to the receiving port 44, such as while the implant 600 is at least partially implanted in the eye.

Some method embodiments can include one or more time points after implantation of the implant 600 at which time the physician can locate the receiving port 44 of the implant 600, such as via an ab externo approach, in order to deliver one or more drugs or other substances to the implant 600. For example, the physician can use a needle or other delivery device to pierce across the sclera and into the implant 600, such as into the receiving port 44. The physician can then deliver one or more drugs or other substances through the receiving port 44 and into the implant 600. The implant 600 can then deliver the one or more drugs or other substances to the eye, such as to the suprachoroidal space. For example, one or more intraocular or intravitreal medications can be delivered to the implant 600, such as via the receiving port 44, at regular or defined time intervals (e.g., once a week, once a month, once every 10 days, etc.).

In some implementations, the implant 600 can include one or more stabilization features, such as wings 46, as shown in FIG. 9. The stabilization features, such as the wings 46, can assist in orienting and maintaining the implant 600 in position relative to its implantation site. This can assist in allowing the receiving port 44 to be accessible, such as with a needle, while the implant 600 is at least partially implanted in the eye. In some implementations, the receiving port 44 can be color coded or marked in such a way that allows a clinician to locate the receiving port. For example, the receiving port 44 can be made out of a radio-opaque material or any material that allows viewing of the material with one or more medical equipment, such as x-ray or ultrasound, for locating the receiving port and properly delivering one or more drugs into the receiving port 44.

The features and profiles of the implants described herein can be formed by one or more of a variety of manufacturing methods. For example, the implant can be formed by laser cutting a tube made out of a medical grade material, such as those discussed above. In addition, the implant can be injection molded. The implant can vary in dimensions in order to accommodate various sized implantation sites and applications. For example, the implant can be approximately 0.15 to 0.35 inches in length, and the extruded features, including rings, can have an outer diameter of approximately 0.010 to 0.030 inches and a length of approximately 0.002 to 0.008 inches. In addition, the large proximal ring can have an outer diameter of approximately 0.01 to 0.03 inches and a length of approximately 0.005 to 0.015 inches. Additionally, the implant body can have an outer diameter of approximately 0.012 to 0.022 inches and an inner diameter of approximately 0.008 to 0.018 inches. Furthermore, the fenestrations can have a diameter of approximately 0.001 to 0.008 inches. The distal end can have a radius of approximately 0.001 to 0.003 inches and the proximal end can have a radius of approximately 0.001 to 0.003 inches.

Figure 10:
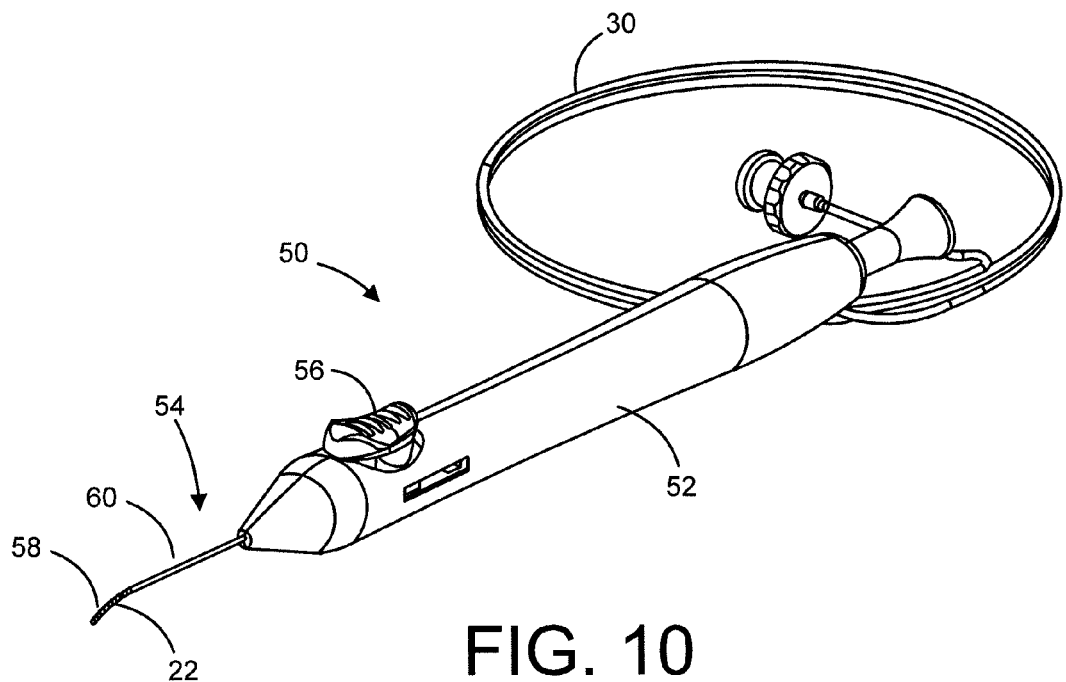
FIG. 10 shows an embodiment of a delivery system, including a delivery device configured to deliver an ocular implant into an eye.

In addition, a delivery system can be used to deliver an implant 20, including at least implants 100, 200, 300, 400, 500 and 600 described herein, into the eye in order to allow the implant 20 to at least provide fluid communication between the anterior chamber and the suprachoroidal or supraciliary space. FIG. 10 shows an embodiment of a delivery system 50 that can be used to deliver the implant 20 into the eye. It should be appreciated that the delivery systems 50 described herein provide some examples, and variations in the structure, shape and actuation of the delivery system 50 are possible.

The delivery system 50 can include a proximal handle component 52 and a distal delivery component 54. The proximal handle component 52 can include an actuator 56, such as a button, to control the release of an implant 20 from the delivery component 54 into the target location in the eye. In addition, the actuator 56 can vary in structure.

An embodiment of the delivery component 54 can include an elongate applier in the form of a guidewire 58 that inserts longitudinally through an internal lumen 21 of the implant 10 and a "stopper" or sheath 60 positioned axially over the guidewire 58. The sheath 60 can aid in the release of the implant 20 from the delivery component 54 into the target location in the eye. The actuator 56 can be used to control movement or relative movement of the guidewire 58 and/or the sheath 60. For example, the sheath 60 can be fixed relative to the handle component 52 and act as a stopper that impedes the implant 20 from moving in a proximal direction as the guidewire 58 is withdrawn proximally from the implant 20 upon actuation of the actuator 56. In a first state, the guidewire 58 can be extended distally relative to the sheath 60. Actuation of the actuator 56, such as by pressing the actuator 56, can cause the guidewire 58 to slide proximally into the sheath 60. This can effectively disengage the implant 20 off the distal end of the guidewire 58 and releases the implant 20 in a controlled fashion such that the target positioning of the implant 20 is maintained.

Figure 11:
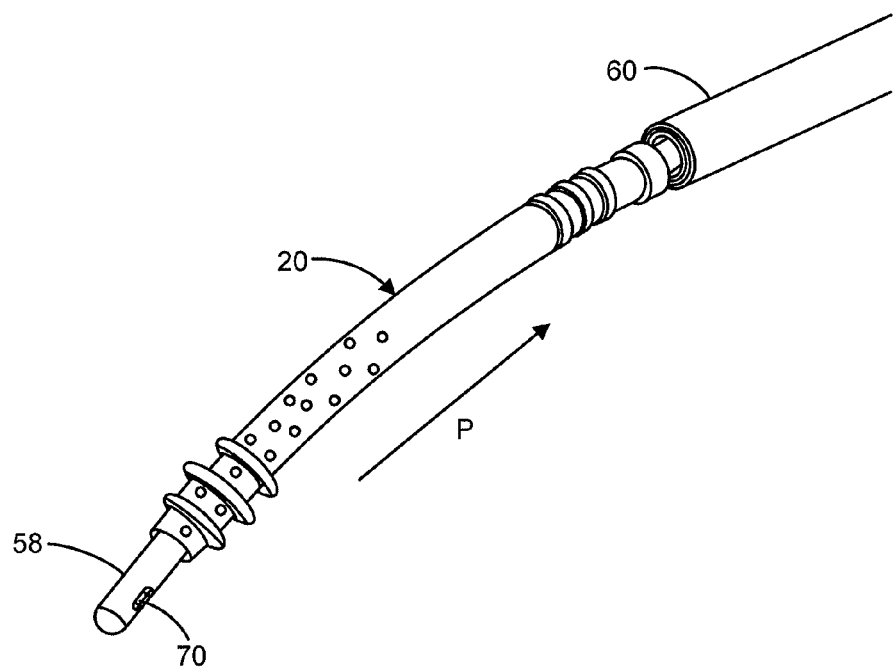
FIG. 11 shows an enlarged view of the delivery system of FIG. 10 showing the ocular implant mounted on a delivery component of the delivery device.

FIG. 11 shows an enlarged view of an implant 20 mounted on a delivery component 54 for inserting the implant 20 into the eye. The implant 20 can be mounted on a distal region of a guidewire 58. The sheath 60 can be sized and shaped to receive or abut a portion of the proximal end of the implant 20. In this embodiment, upon actuation of the actuator 56, the guidewire 58 can slide in the proximal direction (arrow P) into the sheath 60. The proximal end of the implant 20 can abut the distal edge of the sheath 60 to prevent the implant 20 from sliding in the proximal direction. This can effectively disengage the implant 20 off the distal end of the guidewire 58 and controllably release the implant 20 into the eye tissue.

The delivery system 50 can also assist in providing fluid delivery into the eye during or after implantation of the implant 20. The delivered fluid can vary and can include a viscoelastic, drugs, stem cells, or a combination thereof. The delivery of the implant 20 can be in combination with retinal or macula therapy. A fluid delivery feature can include an elongated tube 80 that extends outward from the handle 52. The tube 80 can extend through the handle 52 and can have an internal lumen that communicates at a distal end with the proximal end of an internal lumen in the guidewire 58. One or more outlet openings, such as slots 70, can be located on the distal region of the guidewire 58. The tube 80 can be connected at a proximal end to a source of fluid so as to provide a pathway for the fluid to be delivered to the internal lumen of the guidewire via the tube 80. The fluid can then exit the guidewire via the slots 70 for delivery into the eye.

In alternate embodiments the fluid may be delivered to other sections along the axial length of the implant 20. Fenestrations or holes along the length of the implant 20 may be configured to be sufficiently large such that a fluid may be delivered through corresponding holes along the guidewire 58 and into the eye, such as into the supraciliary or suprachoroidal space surrounding the body of the implant 20, which can depend on where the implant 20 is positioned and the length of the implant 20. This can be advantageous because it can create additional space surrounding the implant 20 and improve tenting.

Figure 12:
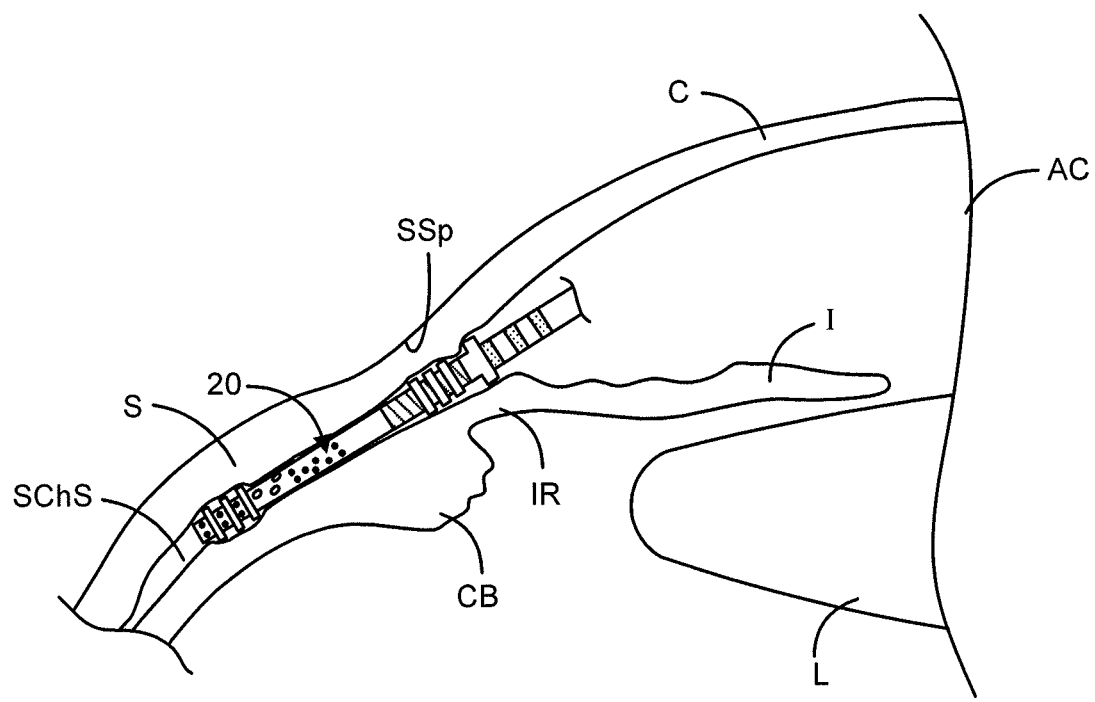
FIG. 12 shows an enlarged view of a section of an eye with an implant mounted on a guidewire approaching an implantation site from an anterior chamber of the eye.

An embodiment of a method of delivering and implanting the implant 20 into the eye includes at least the following description. In general, one or more implants 20 can be slideably loaded on a delivery system 50 and implanted to a position which allows the implant to communicate with at least a part of the anterior chamber and either the suprachoroidal space or supraciliary space, as described herein. The implant 20 can be implanted in the eye via an ab-interno procedure through a limbal incision into the anterior chamber. The implant 20 may then be positioned in the eye so that it provides fluid communication between the anterior chamber and either the suprachoroidal space or supraciliary space, as well as provide increased separation between the sclera and choroid, as shown in FIG. 12.

For example, the guidewire 58 can be positioned on the delivery system 50 such that the distal tip of the guidewire 58, the implant 20 and the sheath 60 can penetrate through a small corneal incision in order to access the anterior chamber, such as within the limbus of the cornea. In an embodiment, the incision can be very close to the limbus, such as either at the level of the limbus or within 2 mm of the limbus in the clear cornea. The guidewire 58 can be used to make the incision or a separate cutting device can be used. For example, a knife-tipped device or diamond knife can be used to provide access into the cornea.

The corneal incision can have a size that is sufficient to permit at least the passage of the implant 20 on the guidewire 58 and sheath 60 therethrough. In at least some method embodiments, the incision can be about 1 mm in size. In another embodiment, the incision is no greater than about 2.5 mm in size. In another embodiment, the incision is no greater than about 2.85 mm and is greater than about 1.5 mm.

After insertion through the incision, the guidewire 58 can be advanced into the anterior chamber along a pathway that enables the implant 20 to be delivered to a position such that the implant 20 provides a flow passageway from the anterior chamber toward either the supraciliary or suprachoroidal space. For example, the guidewire 58 can be advanced further into the eye such that a blunt distal tip of the guidewire 58 and/or the implant 20 can seat with and penetrate at least one of the iris root, a region of the ciliary body, or the iris root part of the ciliary body near its tissue border with the scleral spur.

In some method embodiments, the guidewire 58 can approach the iris root from a same side of the anterior chamber as a deployment location such that the guidewire 58 does not have to be advanced across the iris. Alternately, the guidewire 58 can approach the deployment location from across the anterior chamber such that the guidewire 58 is advanced across the iris and/or the anterior chamber toward the opposite iris root. The guidewire 58 can approach the eye and the iris root along a variety of pathways. In some method embodiments, the guidewire 58 does not cross over the eye and does not intersect an optical axis of the eye. In other words, the corneal incision and the location where the implant 20 can be implanted, such as adjacent the iris root, can be in the same quadrant (for example, if the eye is viewed from the front and divided into four quadrants). Additionally, in some method embodiments, the pathway of the implant from the corneal incision to the iris root does not pass through the optic axis of the eye in order to avoid interfering with the pupil.

FIG. 12 shows an enlarged view of the anterior region of the eye showing the anterior chamber AC, the cornea C, the iris I, and the sclera S. In addition, the implant 20 is shown as mounted on the guidewire 58 and approaching an implantation site from the anterior chamber AC. The implant 20 and guidewire 58 can move along a pathway such that the dissection entry point of the distal tip of the guidewire 58 can penetrate the iris root IR near its junction with the scleral spur SSp or the iris root portion of the ciliary body CB or other desired location. The surgeon can rotate or reposition the handle of the delivery device 50 in order to obtain a proper approach trajectory for the distal tip of the guidewire 58, as described in further detail below.

The guidewire 58 with the implant 20 positioned thereupon can be advanced from a region of the anterior chamber, which can be viewed through a transparent zone of the cornea to a region of the anterior chamber that is obscured by the opaque zone of the cornea. The guidewire 58 and implant 20 can be advanced through the cornea until resistance is felt and a part of the delivery device can be seated at a location near the iris root, the ciliary body or the iris root portion of the ciliary body. The guidewire 58 can then be advanced further such that the guidewire 58 and implant 20 loaded thereon penetrate an area of fibrous attachment between the scleral spur and the ciliary body. This area of fibrous attachment can be approximately 1 mm. Once the distal tip of the guidewire 58 penetrates and is urged past this fibrous attachment region, the guidewire 58 can then more easily cause the sclera to peel away or otherwise separate from the ciliary body and possibly the choroid as it follows the inner curve of the sclera and enters the supraciliary or suprachoroidal space. A combination of the guidewire's tip shape, material, material properties, diameter, flexibility, compliance, coatings, pre-curvature etc. can make it more inclined to follow an implantation pathway that mirrors the curvature of the inner wall of the sclera and between tissue layers, such as between the sclera and the ciliary body and between the sclera and the choroid.

The dissection plane of the guidewire 58 and implant 20 can follow the curve of the inner scleral wall such that the implant 20 mounted on the guidewire 58 after penetrating the iris root or the iris root portion of the ciliary body can bluntly dissect the boundary between tissue layers of the scleral spur and the ciliary body such that at least the distal region of the implant 20 extends into the supraciliary space. In an embodiment, the implant 20 can be positioned such that it extends sufficiently past the scleral spur and is positioned between the tissue boundaries of the sclera and the choroid (the suprachoroidal space SChS).

Once properly positioned, the implant 20 can then be released from the guidewire 58. The implant 20 can be released, for example, by withdrawing the guidewire 58 such that the implant 20 is effectively disengaged in a controlled manner from the tip of the guidewire 58 with the sheath 60.

The implant 20 can include one or more structural features near its proximal region that aid to anchor or retain the implant 20 in the target region in the eye. The structural features can include extruded features, such as rings 28, large proximal rings 34, flanges, protrusions, wings, tines, or prongs, and the like that can lodge into the surrounding eye anatomy to retain the implant 20 in place and prevent the implant 20 from moving further into the suprachoroidal space.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. An ocular implant system for implanting an implant in an eye comprising:
    an elongate tubular body comprising a proximal end, a distal end and an inner lumen extending at least partway between the proximal end and the distal end, the tubular body having a plurality of holes positioned along the length of the tubular body;
    a plurality of fenestrations extending through an outer surface of the tubular body and intersecting with the inner lumen; and
    a plurality of extruded features wherein at least one of the plurality of extruded features extends from the outer surface of the tubular body, and wherein the plurality of extruded features includes a plurality of extruded rings, and wherein each fenestration is positioned immediately adjacent an extruded ring such that each extruded ring immediately adjacent a fenestration tents eye tissue around each fenestration in a manner that results in fluid flow through at least one of the fenestrations when the elongate tubular body is implanted in an eye, and wherein the plurality of extruded rings includes at least one extruded ring positioned at a distal end of the elongate tubular body and at least one extruded ring positioned at a proximal end of the elongate tubular body;
    a delivery device configured to insert the tubular body into the eye, the delivery device including:
        a handle;
        a guidewire that inserts longitudinally through the inner lumen of the tubular body, the guidewire having an interior lumen for passage of fluid and also having a plurality of openings through which fluid can exit the interior lumen of the guidewire;
        a sheath positioned axially over the guidewire and positioned proximal of the tubular body when the tubular body is positioned on the guidewire.

2. The implant of claim 1 wherein the implant is made out of a medical grade material, including at least one of a stainless steel, polyimide, various plastics, or any number of shape memory alloys, including nitinol, and shape memory polymers.

3. The implant of claim 1 wherein at least one of the plurality of extruded features comprises a large proximal ring.

4. The implant of claim 1 wherein the plurality of fenestrations vary in at least one of size and shape.

5. The implant of claim 4 wherein the size of the fenestrations increase along a length of the implant in a distal direction.

6. The implant of claim 4 wherein the fenestrations increase in number along a length of the implant in a distal direction.

7. The implant of claim 1 wherein the plurality of rings vary in at least one of size and shape.

8. The implant of claim 7 wherein the extruded features increase in size along a length of the implant in a distal direction.

9. The implant of claim 1 wherein the implant includes at least one of a beveled proximal end and a beveled distal end.

10. The implant of claim 1 wherein at least one of the proximal end or the distal end includes at least one of a chamfered edge and radiused edge.

11. The implant of claim 1 wherein the implant is at least one of coated with a drug and comprised of a polymer combined with a drug.

12. A method of implanting an implant in an eye, comprising;
    securing an implant to a delivery device configured to insert the implant into the eye, the implant comprising
        an elongate tubular body including a proximal end, a distal end and an inner lumen extending at least partway between the proximal end and the distal end;
        a plurality of fenestrations extending through an outer surface of the tubular body and intersecting with the inner lumen; and
        an a plurality of extruded features extending from the outer surface of the tubular body, and wherein the plurality of extruded features includes a plurality of extruded rings, and wherein each fenestration is positioned immediately adjacent an extruded ring such that each extruded ring immediately adjacent a fenestration tents eye tissue around each fenestration in a manner that results in fluid flow through at least one of the fenestrations when the elongate tubular body is implanted in an eye;
    the delivery device comprising:
        a handle;
        a guidewire that inserts longitudinally through the inner lumen of the tubular body, the guidewire having an interior lumen for passage of fluid and also having a plurality of openings through which fluid can exit the interior lumen of the guidewire;
        a sheath positioned axially over the guidewire and positioned proximal of the tubular body when the tubular body is positioned on the guidewire; and
    inserting the implant into the eye such that each extruded ring tents eye tissue around each of the corresponding fenestrations when the elongate tubular body is implanted in an eye in a manner that results in fluid flow through at least one of the fenestrations.

* * * * *